US007875704B2

(12) United States Patent
Stassen et al.

(10) Patent No.: US 7,875,704 B2
(45) Date of Patent: Jan. 25, 2011

(54) ANTI-PLGF ANTIBODY

(75) Inventors: Jean-Marie Stassen, Lubbeek (BE); Peter Carmeliet, Blanden (BE); Désiré Collen, Winksele (BE)

(73) Assignees: Vlaams Interuniversitair Instituut voor Biotechnologie VZW, Zwijnaarde (BE); Life Sciences Research Partners VZW, Leuven (BE); Thrombogenics N.V., Leuven (BE)

( * ) Notice: Subject to any disclaimer, the term of this patent is extended or adjusted under 35 U.S.C. 154(b) by 382 days.

(21) Appl. No.: 11/909,604

(22) PCT Filed: Mar. 24, 2006

(86) PCT No.: PCT/BE2006/000023

§ 371 (c)(1),
(2), (4) Date: Sep. 24, 2007

(87) PCT Pub. No.: WO2006/099698

PCT Pub. Date: Sep. 28, 2006

(65) Prior Publication Data

US 2008/0193455 A1 Aug. 14, 2008

Related U.S. Application Data

(60) Provisional application No. 60/664,768, filed on Mar. 24, 2005.

(51) Int. Cl.
*C07K 16/00* (2006.01)
(52) U.S. Cl. .................................. 530/387.1; 424/130.1
(58) Field of Classification Search ........................ None
See application file for complete search history.

(56) References Cited

U.S. PATENT DOCUMENTS

| 5,545,806 | A | 8/1996 | Lonberg et al. |
| 5,851,999 | A | 12/1998 | Ullrich et al. |
| 5,919,899 | A | 7/1999 | Persico et al. |
| 2003/0180286 | A1 | 9/2003 | Carmeliet et al. |

FOREIGN PATENT DOCUMENTS

| EP | 1297016 B1 | 3/2006 |
| EP | 1869085 A2 | 12/2007 |
| WO | WO 84/03564 A1 | 9/1984 |
| WO | WO 99/24056 A1 | 5/1999 |
| WO | WO 99/60846 A1 | 12/1999 |
| WO | WO 01/85796 A2 | 11/2001 |
| WO | WO 2006/099698 A2 | 9/2006 |

OTHER PUBLICATIONS

Rudikoff et al. Proc Natl Acad Sci USA 1982 vol. 79 p. 1979.*
MacCallum et al. J. Mol. Biol. (1996) 262, 732-745.*
Pascalis et al. The Journal of Immunology (2002) 169, 3076-3084.*
Casset et al. (2003) BBRC 307, 198-205.*
Vajdos et al. Journal of Molecular Biology. (2002) 320, 415-428.*
Chen et al. J. Mol. Bio. (1999) 293, 865-881.*
Wu et al. J. Mol. Biol. (1999) 294, 151-162.*
Holm et al. Molecular Immunology, (2007) 44, 1075-1084.*
Mueller et al. PNAS vol. 89 pp. 11832-11836, Dec. 1992.*
Attwood (Science 290: 471-473, 2000).*
Skolnick et al. (Trends in Biotech. 18: 34-39, 2000).*
Office Action for European Patent Application No. 06 721 544.2, dated Apr. 15, 2009.
English Language Translation of the Office Action issued in connection with Israeli Patent Application No. 185754, dated Jan. 24, 2010.
Ahmed et al., "Regulation of Placental Vascular Endothelial Growth Factor (VEGF) and Placenta Growth Factor (PlGF) and Soluble Flt-1 by Oxygen—A Review," *Placenta* 21(Suppl. A):S16-S24, 2000.
Barillari et al., "The Basic Residues of Placenta Growth Factor Type 2 Retrieve Sequestered Angiogenic Factors into a Soluble Form," *Am. J. Pathol.* 152:1161-1166, 1998.
Bernatchez et al., "Vascular Endothelial Growth Factor Effect on Endothelial Cell Proliferation, Migration, and Platelet-Activating Factor Synthesis Is Flk-1-Dependent," *J. Biol. Chem.* 274:31047-31054, 1999.
Bicknell et al., "Introduction," in *Tumor Angiogenesis*, Ed. Bicknell et al., Oxford University Press Inc., New York, NY, pp. 1-3, 1997.
Bottomley et al., "Placenta Growth Factor (PlGF) Induced Vascular Endothelial Growth Factor (VEGF) Secretion from Mononuclear Cells and Is Co-Expressed with VEGF in Synovial Fluid," *Clin. Exp. Immunol.* 119:182-188, 2000.
Brenchley, "Angiogenesis in Inflammatory Joint Disease: A Target for Therapeutic Intervention," *Clin. Exp. Immunol.* 121:426-429, 2000.
Carmeliet, "Molecular Mechanisms of Normal and Pathologic Angiogenesis: Insights and Therapeutic Concepts from Transgenic Mice," *J. Vasc. Res.* 37(Suppl. 1):79, 2000. Abstract No. 46.
Carmeliet, "Mechanisms of Angiogenesis and Arteriogenesis," *Nature Medicine* 6:389-395, 2000.
Christinger et al., "The Crystal Structure of Placental Growth Factor in Complex with Domain 2 of Vascular Endothelial Growth Factor Receptor-1," *J. Biol. Chem.* 279:10382-10388, 2004.
Colucciello, "Proliferative Diabetic Retinopathy," *Postgraduate Medicine Online*, vol. 116, No. 1, 2004 (http://www.postgradmed.com.issues/2004/07_04/colucciello.htm).
Declerck et al., "Generation of Monoclonal Antibodies Against Autologous Proteins in Gene-Inactivated Mice," *J. Biol. Chem.* 270:8397-8400, 1995.
Donnini et al., "Expression and Localization of Placenta Growth Factor and PlGF Receptors in Human Meningiomas," *J. Pathol.* 189:66-71, 1999.
Fan et al., "In Vivo Models of Angiogenesis," in *Tumor Angiogenesis*, Ed. Bicknell et al., Oxford University Press Inc., New York, NY, pp. 5-18, 1997.
Fidler et al., "Biology of Cancer: Angiogenesis," in Cancer: Principles & Practice of Oncology, 6th Edition, Ed. DeVita Jr. et al., Lippincott, Williams & Wilkins, Philadelphia, PA, pp. 137-147, 2001.

(Continued)

*Primary Examiner*—Misook Yu
*Assistant Examiner*—Meera Natarajan
(74) *Attorney, Agent, or Firm*—Clark & Elbing LLP

(57) ABSTRACT

The present invention provides novel monoclonal antibodies directed to PlGF and fragments and derivatives thereof, more particularly to humanized antibodies and fragments thereof for use in the treatment and/or prevention of pathological angiogenesis.

17 Claims, 15 Drawing Sheets

OTHER PUBLICATIONS

Fischer et al., "Anti-PlGF Inhibits Growth of VEGF(R)-Inhibitor-Resistant Tumors Without Affecting Healthy Vessels," *Cell* 131:463-475, 2007.
Folkman, "Clinical Applications of Research on Angiogenesis," *N. Eng. J. Med.* 333:1757-1763, 1995.
Griffioen et al., "Angiogenesis: Potentials for Pharmacologic Intervention in the Treatment of Cancer, Cardiovascular Diseases, and Chronic Inflammation," *Pharmacol. Reviews* 52:237-268, 2000.
Guidi et al., "Expression of Vascular Permeability Factor (Vascular Endothelial Growth Factor) and Its Receptors in Endometrial Carcinoma," *Cancer* 78:454-460, 1996.
Gura et al., Systems for Identifying New Drugs Are Often Faulty, *Science* 278:1041-1042, 1997.
Hansma et al., "Recombinant Human Endostatin Administered as a 28-Day Continuous Intravenous Infusion, Followed by Daily Subcutaneous Injections: A Phase I and Pharmacokinetic Study in Patients with Advanced Cancer," *Ann. Oncol.* 16:1695-1701, 2005.
Hazelton et al., "Vascular Endothelial Growth Factor in Ovarian Cancer," *Current Oncol. Reports* 1:59-63, 1999.
Inoue et al., "Mechanism of Mustard Oil-Induced Skin Inflammation in Mice," *Eur. J. Pharmacol.* 333:231-240, 1997.
Jain et al., "AlphaPlGF: A New Kid on the Antiangiogenesis Block," *Cell* 131:443-445, 2007.
Johnstone et al., *Immunochemistry in Practice*, Blackwell Scientific Publications, Oxford, p. 30, 1987.
Kanno et al., "Roles of Two VEGF Receptors, Flt-1 and KDR, in the Signal Transduction of VEGF Effects in Human Vascular Endothelial Cells," *Oncogene* 19:2138-2146, 2000.
Katoh et al., "Expression of Vascular Endothelial Growth Factor (VEGF) in Human Thyroid Neoplasms," *Human Pathol.* 30:891-897, 1999.
Köhler et al., "Continuous Cultures of Fused Cells Secreting Antibody of Predefined Specificity," *Nature* 256:495-497, 1975.
Luttun et al., "Genetic Dissection of Tumor Angiogenesis: Are P1GF and VEGFR-1 Novel Anti-Cancer Targets?" *Biochim. Biophys. Acta* 1654:79-94, 2004.
Maglione et al., "Isolation of a Human Placenta cDNA Coding for a Protein Related to the Vascular Permeability Factor," *Proc. Natl. Acad. Sci. U.S.A.* 88:9267-9271, 1991.
Maglione et al., "Two Alternative mRNA Coding for the Angiogenic Factor, Placenta Growth Factor (PlGF), Are Transcribed from a Single Gene of Chromosome 14," *Oncogene* 8:925-931, 1993.
Maragoudakis, "Introductory Comments," in *Advances in Experimental Medicine* and Biology, vol. 476: *Angiogenesis from the Molecular to Integrative Pharmacology*, Ed. Maragoudakis, Kluwer Academic/Plenum Publishers, Boston, MA, pp. 1-4, 2000.
Migdal et al., "Neurophilin-1 Is a Placenta Growth Factor-2 Receptor," *J. Biol. Chem.* 273:22272-22278, 1998.
Miller, "Issues and Challenges for Antiangiogenic Therapies," *Breast Cancer Res. Treat.* 75(Suppl. 1):S45-S50, 2002.
MSNBC News Services, "Mixed Results on New Cancer Drug," Nov. 9, 2000.
Nicol et al., "Vascular Endothelial Growth Factor Expression Is Increased in Renal Cell Carcinoma," *J. Urology* 157:1482-1486, 1997.
Nomura et al., "Placenta Growth Factor (PlGF) mRNA Expression in Brain Tumors," *J. Neuro-Oncol.* 40:123-130, 1998.
Oliver et al., "Suppression of Collagen-Induced Arthritis by an Angiogenesis Inhibitor, AGM-1470, in Combination with Cyclosporin: Reduction of Vascular Endothelial Growth Factor (VEGF)," *Cell. Immunol.* 166:196-206, 1995.
Paleolog et al., "Angiogenesis in Arthritis: Role in Disease Pathogenesis and as a Potential Therapeutic Target," *Angiogenesis* 2:295-307, 1999.
Paques et al., "Growth Factors and Diabetic Retinopathy," *Diabetes Metabol.* 23:125-130, 1997.
Park et al., "Potentiation of Vascular Endothelial Growth Factor Bioactivity, In Vitro and In Vivo, and High Affinity Binding to Flt-1 But Not to Flk-1/KDR," *J. Biol. Chem.* 269:25646-25654, 1994.
Parry et al., "Bioactivity of Anti-Angiogenic Ribozymes Targeting Flt-1 and KDR mRNA," *Nucleic Acids Res.* 27:2569-2577, 1999.

Queen et al., "A Humanized Antibody that Binds to Interleukin 2 Receptor," *Proc. Natl. Acad. Sci. U.S.A.* 86:10029-10033, 1989.
Research and Development Systems, Inc., "Monoclonal Anti-Mouse PlGF-2 Antibody," Catalog No. MAB465, Oct. 18, 1999.
Research and Development Systems, Inc., "Biotinylated Anti-Mouse PlGF-2 Antibody," Catalog No. BAF465, Jan. 21, 1999.
Ryan et al., "Preclinical Safety Evaluation of rhuMAbVEGF, an Antiangiogenic Humanized Monoclonal Antibody," *Toxicol. Pathol.* 27:78-86, 1999.
Takahashi et al., "Markedly Increased Amounts of Messenger RNAs for Vascular Endothelial Growth Factor and Placenta Growth Factor in Renal Cell Carcinoma Associated with Angiogenesis," *Cancer Res.* 54:4233-4237, 1994.
Viglietto et al., "Upregulation of Vascular Endothelial Growth Factor (VEGF) and Downregulation of Placenta Growth Factor (PlGF) Associated with Malignancy in Human Thyroid Tumors and Cell Lines," *Oncogene* 11:1569-1579, 1995.
Viglietto et al., "Neovascularization in Human Germ Cell Tumors Correlates with a Marked Increase in the Expression of the Vascular Endothelial Growth Factor But Not the Placenta-Derived Growth Factor," *Oncogene* 13:577-587, 1996.
Weindel et al., "Detection and Quantification of Vascular Endothelial Growth Factor/Vascular Permeability Factor in Brain Tumor Tissue and Cyst Fluid: the Key to Angiogenesis?" *Neurosurgery* 35:439-449, 1994.
Yonekura et al., "Placenta Growth Factor and Vascular Endothelial Growth Factor B and C Expression in Microvascular Endothelial Cells and Pericytes," *J. Biol. Chem.* 274:35172-35178, 1999.
Ziche et al., "Placenta Growth Factor-1 Is Chemotactic, Mitogenic, and Angiogenic," *Lab. Invest.* 76:517-531, 1997.
Statement from Professor Bengt Fagrell, Organizer of the European Conference on Microcirculation of 2000, dated Mar. 3, 2005.
Statement from Isabelle Flückiger of the Karger Publishing Company, dated Feb. 7, 2005.
International Search Report for PCT/BE2006/000023, completed Sep. 5, 2006.
Written Opinion of the International Searching Authority for PCT/BE2006/000023, completed Sep. 5, 2006.
International Preliminary Report on Patentability for PCT/BE2006/000023, completed Mar. 20, 2007.
International Search Report for PCT/EP2001/05478, completed Sep. 18, 2001.
International Preliminary Report on Patentability for PCT/EP2001/05478, completed Apr. 9, 2002.
Examination Report for EP 01943357.2-2401, dated Jul. 9, 2003.
Reply to Examination Report (Jul. 9, 2003) for EP 01943357.2-2401, dated Nov. 3, 2003.
Examination Report for EP 01943357.2-2401, dated Dec. 1, 2003.
Reply to Examination Report (Dec. 1, 2003) for EP 01943357.2-2401, dated Apr. 15, 2004.
Examination Report for EP 01943357.2-2401, dated Apr. 30, 2004.
Reply to Examination Report (Apr. 30, 2004) for EP 01943357.2-2401, dated Oct. 27, 2004.
Summons to Attend Oral Proceedings for EP 01943357.2-2401, dated Dec. 29, 2004.
Written Submission in Response to Summons to Attend Oral Proceedings for EP 01943357.2-2401, dated Mar. 24, 2005.
Auxillary Request for EP 01943357.2-2401, dated Apr. 22, 2005.
Examination Report for EP 01943357.2-2401, dated May 2, 2005.
Reply to Examination Report (May 2, 2005) for EP 01943357.2-2401, dated Sep. 5, 2005.
Communication of Notice of Opposition for EP 01943357.2-2401, dated Jan. 9, 2007.
Reply to Communication of Notice of Opposition for EP 01943357.2-2401, dated Sep. 28, 2007.
Office Action (U.S. Appl. No. 10/291,979), mailed Nov. 1, 2005.
Office Action (U.S. Appl. No. 10/291,979), mailed Nov. 30, 2006.
Office Action (U.S. Appl. No. 10/291,979), mailed Oct. 11, 2007.
Office Action (U.S. Appl. No. 10/291,979), mailed Jul. 25, 2008.
Notice of Allowance (U.S. Appl. No. 10/291,979), mailed Oct. 31, 2008.
Notice of Allowance (U.S. Appl. No. 10/291,979), mailed Dec. 15, 2008.

Office Action for Chinese Patent Application No. 200680009327.9, dated May 21, 2010.
English Translation of Office Action for Chinese Patent Application No. 200680009327.9, dated May 21, 2010.

Examination Report for Australian Patent Application No. 2006227571, dated Sep. 6, 2010.

* cited by examiner

A
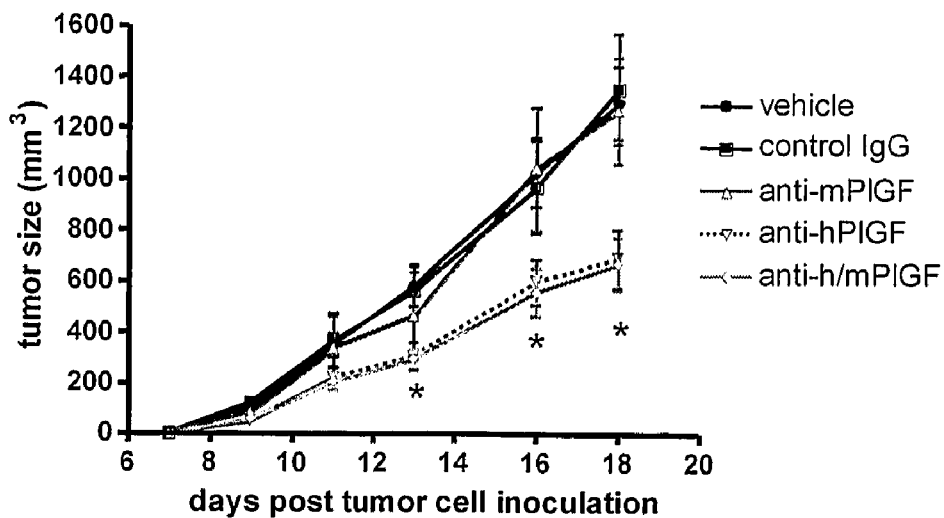
B
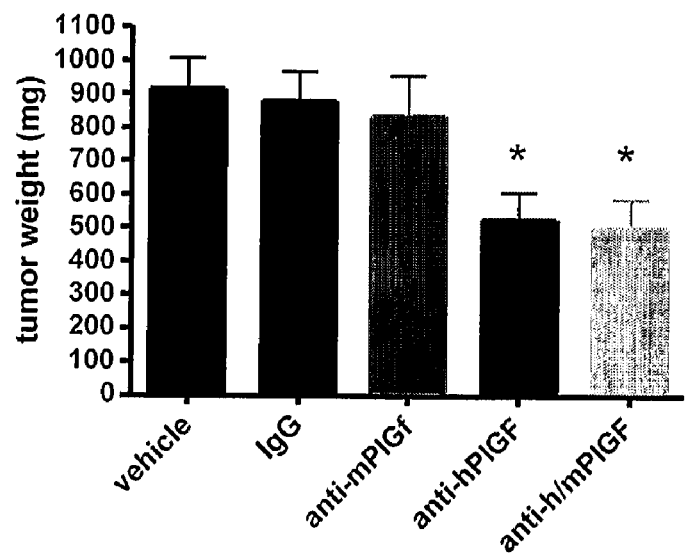
Figure 4

A
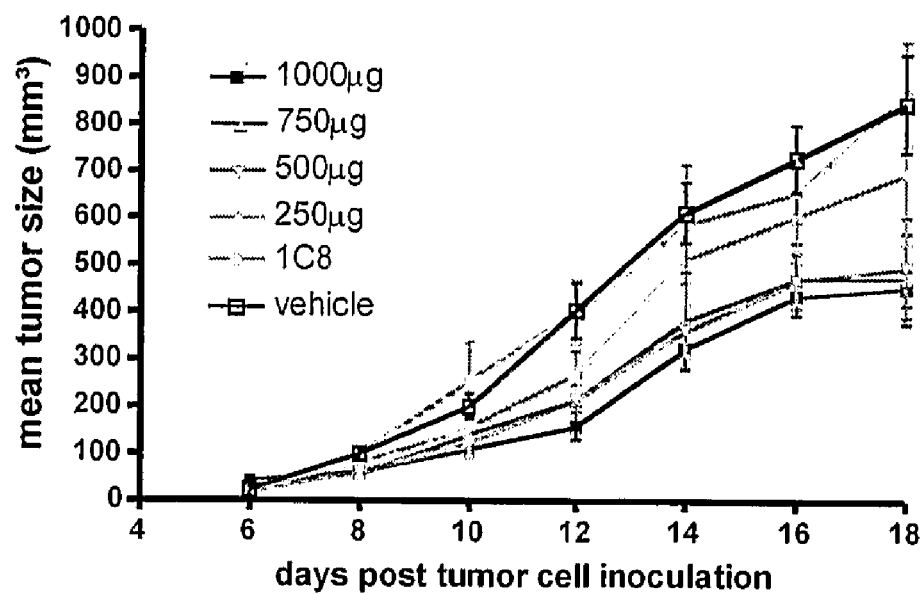
B
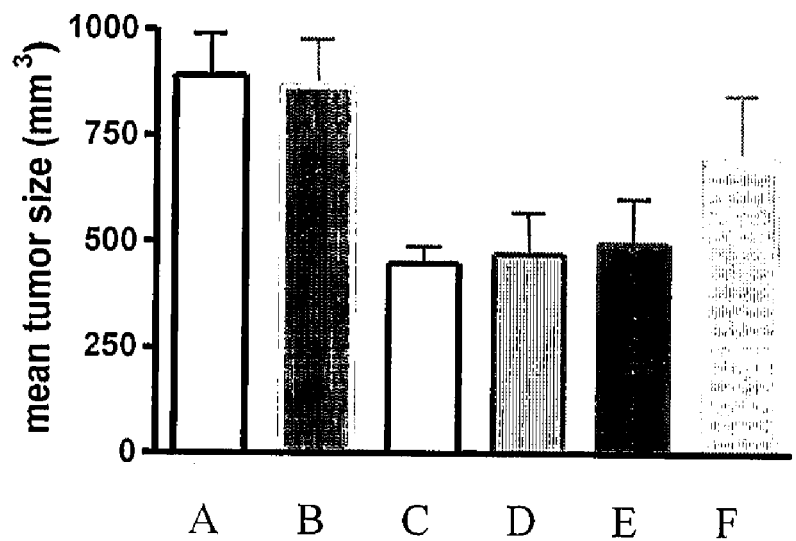
Figure 5

A
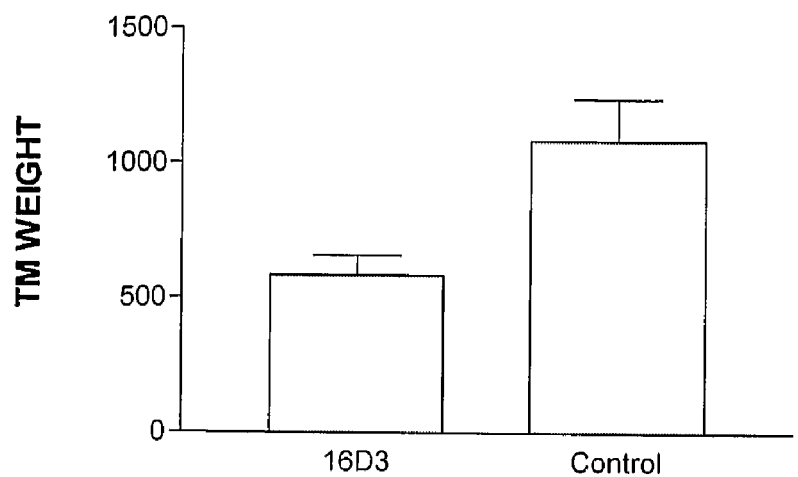
B
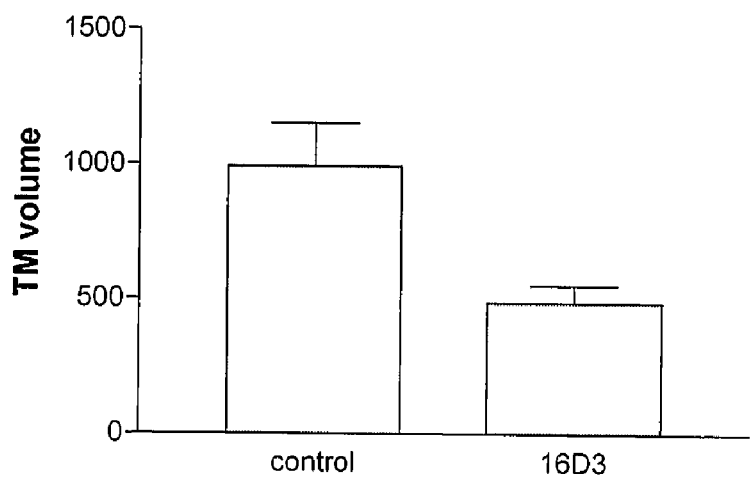
Figure 6

A
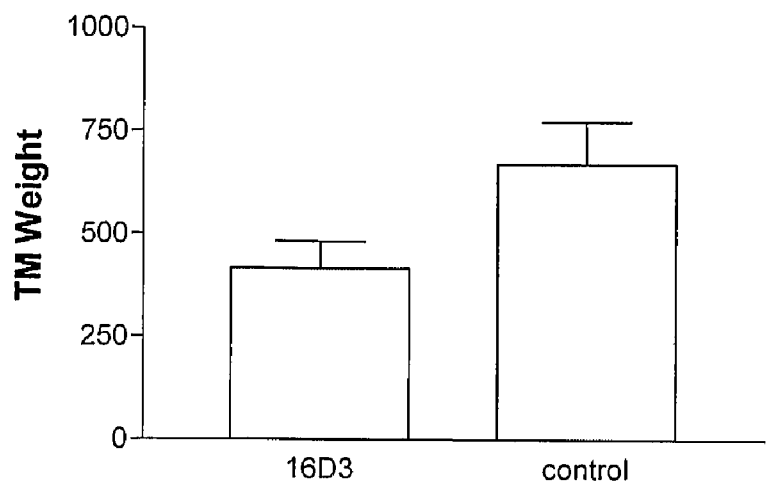
B
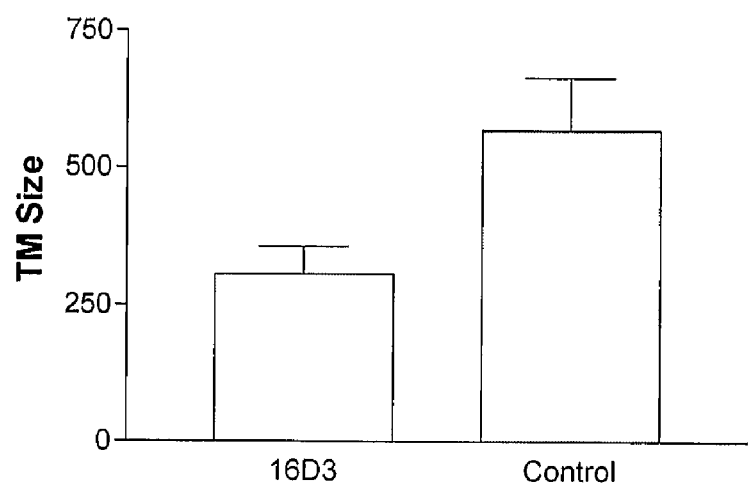
Figure 7

A: DNA sequence of the mouse variable part of the heavy chain (SEQ ID NO: 1)

```
cagatccagctgcagcagtctggacctgagctggtgaagcctggggcttcagtgaagatatc
ctgcaaggcctctggctacaccttcactgactactatataaactgggtgaagttgaagcctg
gacagggacttgagtggattggatggatttatcctggaagcggtaatactaagtacaatgag
aagttcaagggcaaggccacattgactatagacacatcctccagcacagcctacatgcagct
cagcagcctgacatctgaggacactgctgtctatttctgtgtaagagacagccctttctttg
actactggggccaaggcaccactctcacagtctcctca
```

B: DNA sequence of the mouse variable part of the light chain (SEQ ID NO: 3):

```
gacattgtgctgtcacagtctccatcctccctggctgtgtcagcaggagagaaggtcactat
gcgctgcaaatccagtcagagtctgctcaacagtggaatgcgaaagagtttcttggcttggt
accagcagaaaccagggcagtctcctaagctgctgatctactgggcatccactagggaatct
ggggtccctgatcgcttcacaggcagtggatctgggacagatttcactctcaccatcagcag
tgtgcaggctgaagacctggcagtttattactgcaagcaatcttatcatctattcacgttcg
gctcggggacaaagttggaaataaaa
```

C: AA sequence of the mouse variable part of the heavy chain (SEQ ID NO: 2):

QIQLQQSGPELVKPGASVKISCKASGYTFTDYYINWVKLKPGQGLEWIGWIYPGSGN
TKYNEKFKGKATLTIDTSSSTAYMQLSSLTSEDTAVYFCVRDSPFFDYWGQGTTLTV
SS

D: AA sequence of the mouse variable part of the light chain (SEQ ID NO: 4)

DIVLSQSPSSLAVSAGEKVTMRCKSSQSLLNSGMRKSFLAWYQQKPGQSPKLLIYWA
STRESGVPDRFTGSGSGTDFTLTISSVQAEDLAVYYCKQSYHLFTFGSGTKLEIK

Figure 11

A. DNA sequence of the humanised variable part of the heavy chain (SEQ ID NO: 5):

caggtccagctgcagcagtctggagccgagctggtgaagcctggggcttcagtgaagatatc
ctgcaaggcctctggctacaccttcactgactactatataaactgggtgaagttggcccctg
gacagggacttgagtggattggatggatttatcctggaagcggtaatactaagtacaatgag
aagttcaagggcaaggccacattgactatagacacatcctccagcacagcctacatgcagct
cagcagcctgacatctgaggacactgctgtctatttctgtgtaagagacagcccttttctttg
actactggggccaaggcaccctgctcacagtctcctca B. DNA sequence of the humanised variable part of the light chain (SEQ ID NO: 7):

gacattgtgctgacccagtctccagactccctggctgtgtcactgggagagcgggtcactat
gaactgcaaatccagtcagagtctgctcaacagtggaatgcgaaagagtttcttggcttggt
accagcagaaaccagggcagtctcctaagctgctgatctactgggcatccactagggaatct
ggggtccctgatcgcttcacaggcagtggatctgggacagatttcactctcaccatcagcag
tgtgcaggctgaagacgtcgcagtttattactgcaagcaatcttatcatctattcacgttcg
gctcggggacaaagttggaaataaaa C. AA sequence of the humanised variable part of the heavy chain (SEQ ID NO: 6):

QVQLQQSGAELVKPGASVKISCKASGYTFTDYYINWVKLAPGQGLEWIGWIYPGSGN
TKYNEKFKGKATLTIDTSSSTAYMQLSSLTSEDTAVYFCVRDSPFFDYWGQGTLLTV
SS

D. AA sequence of the humanised variable part of the light chain (SEQ ID NO: 8):

DIVLTQSPDSLAVSLGERVTMNCKSSQSLLNSGMRKSFLAWYQQKPGQSPKLLIYWA
STRESGVPDRFTGSGSGTDFTLTISSVQAEDVAVYYCKQSYHLFTFGSGTKLEIK

Figure 12

A
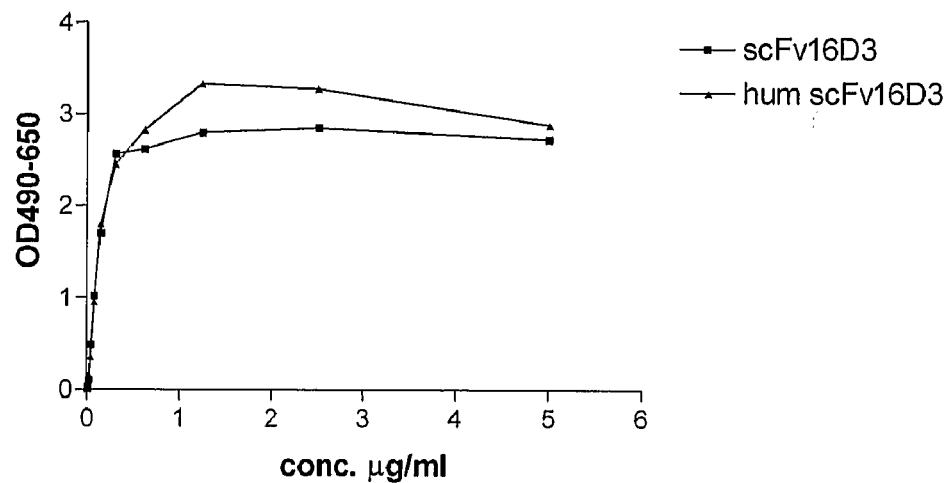
B
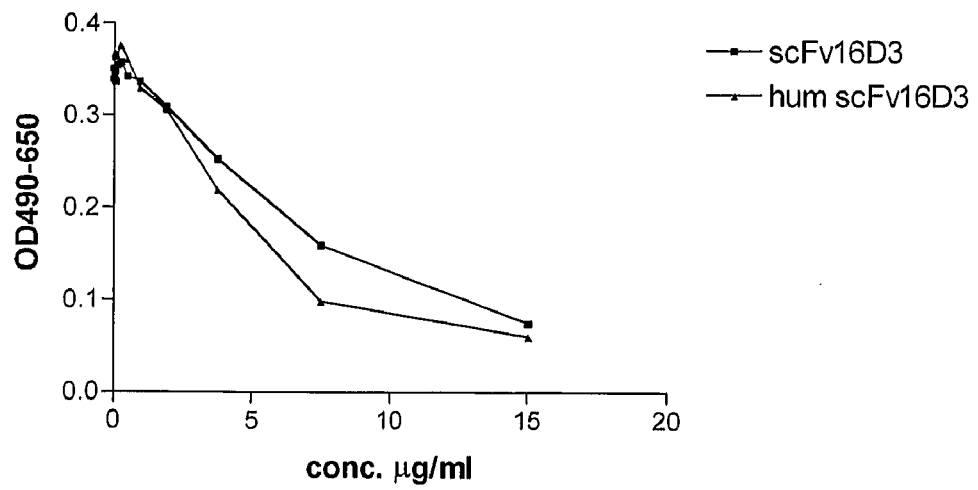
Figure 14

A

```
QIQLQQSGPE LVKPGASVKI SCKASGYTFT DYYINWVKLK PGQGLEWIGW  50
IYPGSGNTKY NEKFKGKATL TIDTSSSTAY MQLSSLTSED TAVYFCVRDS 100
PFFDYWGQGT TLTVSSGGGG SGGGGSGGGG SDIVLSQSPS SLAVSAGEKV 150
TMRCKSSQSL LNSGMRKSFL AWYQQKPGQS PKLLIYWAST RESGVPDRFT 200
GSGSGTDFTL TISSVQAEDL AVYYCKQSYH LFTFGSGTKL EIKGSYPYDV 250
PDYAGSHHHH HH
```

Heavy chain        :AA 1-116
Linker sequence    :AA 117-131
Light chain        :AA 132-243
HA-tag             :AA 246-254
His Tag            :AA 256-262

[SEQ ID No:24]

B

```
QVQLQQSGAE LVKPGASVKI SCKASGYTFT DYYINWVKLA PGQGLEWIGW  50
IYPGSGNTKY NEKFKGKATL TIDTSSSTAY MQLSSLTSED TAVYFCVRDS 100
PFFDYWGQGT LLTVSSGGGG SGGGGSGGGG SDIVLTQSPD SLAVSLGERV 150
TMNCKSSQSL LNSGMRKSFL AWYQQKPGQS PKLLIYWAST RESGVPDRFT 200
GSGSGTDFTL TISSVQAEDV AVYYCKQSYH LFTFGSGTKL EIKGSYPYDV 250
PDYAGSHHHH HH
```

Heavy chain        :AA 1-116
Linker sequence    :AA 117-131
Light chain        :AA 132-243
HA-tag             :AA 246-254
His Tag            :AA 256-262

[SEQ ID NO: 26]

Figure 15

A
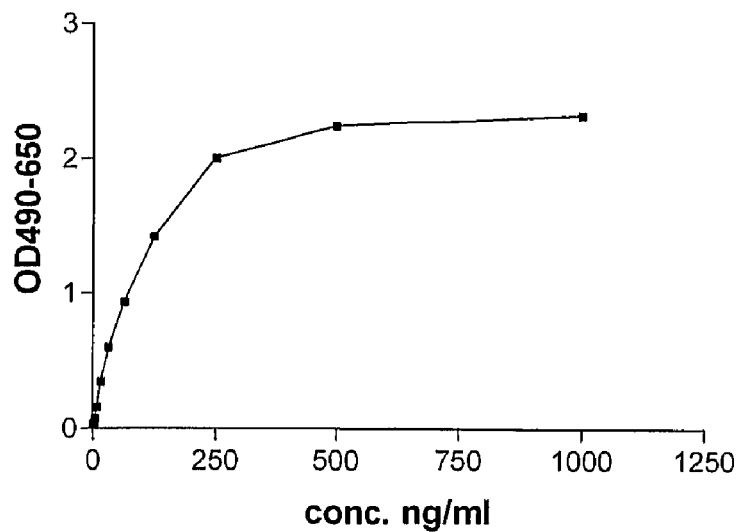
B
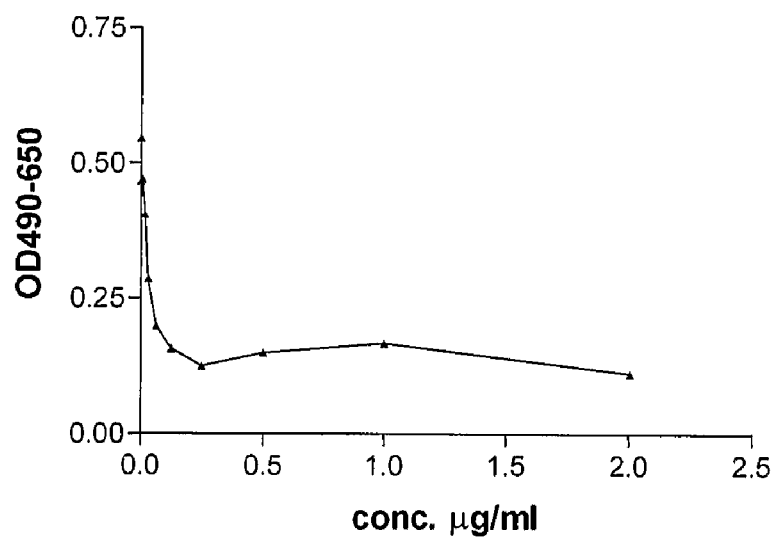
Figure 17

```
                        SEQUENCE LISTING

<160> NUMBER OF SEQ ID NOS: 30

<210> SEQ ID NO 1
<211> LENGTH: 348
<212> TYPE: DNA
<213> ORGANISM: Mus musculus
<220> FEATURE:
<221> NAME/KEY: CDS
<222> LOCATION: (1)..(348)
<223> OTHER INFORMATION: mouse variable part of the heavy chain of 16D3

<400> SEQUENCE: 1 cag atc cag ctg cag cag tct gga cct gag ctg gtg aag cct ggg gct       48
Gln Ile Gln Leu Gln Gln Ser Gly Pro Glu Leu Val Lys Pro Gly Ala
1               5                   10                  15 tca gtg aag ata tcc tgc aag gcc tct ggc tac acc ttc act gac tac       96
Ser Val Lys Ile Ser Cys Lys Ala Ser Gly Tyr Thr Phe Thr Asp Tyr
            20                  25                  30 tat ata aac tgg gtg aag ttg aag cct gga cag gga ctt gag tgg att      144
Tyr Ile Asn Trp Val Lys Leu Lys Pro Gly Gln Gly Leu Glu Trp Ile
        35                  40                  45 gga tgg att tat cct gga agc ggt aat act aag tac aat gag aag ttc      192
Gly Trp Ile Tyr Pro Gly Ser Gly Asn Thr Lys Tyr Asn Glu Lys Phe
    50                  55                  60 aag ggc aag gcc aca ttg act ata gac aca tcc tcc agc aca gcc tac      240
Lys Gly Lys Ala Thr Leu Thr Ile Asp Thr Ser Ser Ser Thr Ala Tyr
65                  70                  75                  80 atg cag ctc agc agc ctg aca tct gag gac act gct gtc tat ttc tgt      288
Met Gln Leu Ser Ser Leu Thr Ser Glu Asp Thr Ala Val Tyr Phe Cys
                85                  90                  95 gta aga gac agc cct ttc ttt gac tac tgg ggc caa ggc acc act ctc      336
Val Arg Asp Ser Pro Phe Phe Asp Tyr Trp Gly Gln Gly Thr Thr Leu
            100                 105                 110 aca gtc tcc tca                                                      348
Thr Val Ser Ser
        115
```

<210> SEQ ID NO 2
<211> LENGTH: 116
<212> TYPE: PRT
<213> ORGANISM: Mus musculus

<400> SEQUENCE: 2

Gln Ile Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Tyr
            20                  25                  30

Tyr Ile Asn Trp Val Lys Leu Lys Pro Gly Gln Gly Leu Glu Trp Ile
        35                  40                  45

Gly Trp Ile Tyr Pro Gly Ser Gly Asn Thr Lys Tyr Asn Glu Lys Phe
    50                  55                  60

Lys Gly Lys Ala Thr Leu Thr Ile Asp Thr Ser Ser Thr Ala Tyr
65                  70                  75                  80

Met Gln Leu Ser Ser Leu Thr Ser Glu Asp Thr Ala Val Tyr Phe Cys
                85                  90                  95

Val Arg Asp Ser Pro Phe Phe Asp Tyr Trp Gly Gln Gly Thr Thr Leu
            100                 105                 110

Thr Val Ser Ser
        115

<210> SEQ ID NO 3
<211> LENGTH: 336
<212> TYPE: DNA
<213> ORGANISM: Mus musculus
<220> FEATURE:
<221> NAME/KEY: CDS
<222> LOCATION: (1)..(336)
<223> OTHER INFORMATION: mouse variable part of the light chain of 16D3

<400> SEQUENCE: 3 gac att gtg ctg tca cag tct cca tcc tcc ctg gct gtg tca gca gga        48
Asp Ile Val Leu Ser Gln Ser Pro Ser Ser Leu Ala Val Ser Ala Gly
1               5                   10                  15 gag aag gtc act atg cgc tgc aaa tcc agt cag agt ctg ctc aac agt        96
Glu Lys Val Thr Met Arg Cys Lys Ser Ser Gln Ser Leu Leu Asn Ser
            20                  25                  30 gga atg cga aag agt ttc ttg gct tgg tac cag cag aaa cca ggg cag       144
Gly Met Arg Lys Ser Phe Leu Ala Trp Tyr Gln Gln Lys Pro Gly Gln
        35                  40                  45 tct cct aag ctg ctg atc tac tgg gca tcc act agg gaa tct ggg gtc       192
Ser Pro Lys Leu Leu Ile Tyr Trp Ala Ser Thr Arg Glu Ser Gly Val
    50                  55                  60 cct gat cgc ttc aca ggc agt gga tct ggg aca gat ttc act ctc acc       240
Pro Asp Arg Phe Thr Gly Ser Gly Ser Gly Thr Asp Phe Thr Leu Thr
65                  70                  75                  80 atc agc agt gtg cag gct gaa gac ctg gca gtt tat tac tgc aag caa       288
Ile Ser Ser Val Gln Ala Glu Asp Leu Ala Val Tyr Tyr Cys Lys Gln
                85                  90                  95 tct tat cat cta ttc acg ttc ggc tcg ggg aca aag ttg gaa ata aaa       336
Ser Tyr His Leu Phe Thr Phe Gly Ser Gly Thr Lys Leu Glu Ile Lys
            100                 105                 110

<210> SEQ ID NO 4
<211> LENGTH: 112
<212> TYPE: PRT
<213> ORGANISM: Mus musculus

<400> SEQUENCE: 4

Asp Ile Val Leu Ser Gln Ser Pro Ser Ser Leu Ala Val Ser Ala Gly
1               5                   10                  15

Glu Lys Val Thr Met Arg Cys Lys Ser Gln Ser Leu Leu Asn Ser
            20                  25                  30

Gly Met Arg Lys Ser Phe Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Ser Tyr His Leu Phe Thr Phe Gly Ser Gly Thr Lys Leu Glu Ile Lys
            100                 105                 110

<210> SEQ ID NO 5
<211> LENGTH: 348
<212> TYPE: DNA
<213> ORGANISM: Artificial sequence
<220> FEATURE:
<223> OTHER INFORMATION: Humanised antibody fragment
<220> FEATURE:
<221> NAME/KEY: CDS
<222> LOCATION: (1)..(348)
<223> OTHER INFORMATION: humanised variable part of the heavy chain of
      16D3

<400> SEQUENCE: 5 cag gtc cag ctg cag cag tct gga gcc gag ctg gtg aag cct ggg gct     48
Gln Val Gln Leu Gln Gln Ser Gly Ala Glu Leu Val Lys Pro Gly Ala
1               5                   10                  15 tca gtg aag ata tcc tgc aag gcc tct ggc tac acc ttc act gac tac     96
Ser Val Lys Ile Ser Cys Lys Ala Ser Gly Tyr Thr Phe Thr Asp Tyr
            20                  25                  30 tat ata aac tgg gtg aag ttg gcc cct gga cag gga ctt gag tgg att    144
Tyr Ile Asn Trp Val Lys Leu Ala Pro Gly Gln Gly Leu Glu Trp Ile
        35                  40                  45 gga tgg att tat cct gga agc ggt aat act aag tac aat gag aag ttc    192
Gly Trp Ile Tyr Pro Gly Ser Gly Asn Thr Lys Tyr Asn Glu Lys Phe
    50                  55                  60 aag ggc aag gcc aca ttg act ata gac aca tcc tcc agc aca gcc tac    240
Lys Gly Lys Ala Thr Leu Thr Ile Asp Thr Ser Ser Ser Thr Ala Tyr
65                  70                  75                  80 atg cag ctc agc agc ctg aca tct gag gac act gct gtc tat ttc tgt    288
Met Gln Leu Ser Ser Leu Thr Ser Glu Asp Thr Ala Val Tyr Phe Cys
                85                  90                  95 gta aga gac agc cct ttc ttt gac tac tgg ggc caa ggc acc ctg ctc    336
Val Arg Asp Ser Pro Phe Phe Asp Tyr Trp Gly Gln Gly Thr Leu Leu
            100                 105                 110 aca gtc tcc tca                                                    348
Thr Val Ser Ser
            115

<210> SEQ ID NO 6
<211> LENGTH: 116
<212> TYPE: PRT
<213> ORGANISM: Artificial sequence
<220> FEATURE:
<223> OTHER INFORMATION: Synthetic Construct

<400> SEQUENCE: 6

```
Gln Val Gln Leu Gln Gln Ser Gly Ala Glu Leu Val Lys Pro Gly Ala
1               5                   10                  15

Ser Val Lys Ile Ser Cys Lys Ala Ser Gly Tyr Thr Phe Thr Asp Tyr
            20                  25                  30

Tyr Ile Asn Trp Val Lys Leu Ala Pro Gly Gln Gly Leu Glu Trp Ile
        35                  40                  45

Gly Trp Ile Tyr Pro Gly Ser Gly Asn Thr Lys Tyr Asn Glu Lys Phe
    50                  55                  60

Lys Gly Lys Ala Thr Leu Thr Ile Asp Thr Ser Ser Thr Ala Tyr
65                  70                  75                  80

Met Gln Leu Ser Ser Leu Thr Ser Glu Asp Thr Ala Val Tyr Phe Cys
                85                  90                  95

Val Arg Asp Ser Pro Phe Phe Asp Tyr Trp Gly Gln Gly Thr Leu Leu
                100                 105                 110

Thr Val Ser Ser
        115
```

<210> SEQ ID NO 7
<211> LENGTH: 336
<212> TYPE: DNA
<213> ORGANISM: Artificial sequence
<220> FEATURE:
<223> OTHER INFORMATION: Humanised antibody fragment
<220> FEATURE:
<221> NAME/KEY: CDS
<222> LOCATION: (1)..(336)
<223> OTHER INFORMATION: humanised variable part of the light chain of 16D3

<400> SEQUENCE: 7

```
gac att gtg ctg acc cag tct cca gac tcc ctg gct gtg tca ctg gga    48
Asp Ile Val Leu Thr Gln Ser Pro Asp Ser Leu Ala Val Ser Leu Gly
1               5                   10                  15 gag cgg gtc act atg aac tgc aaa tcc agt cag agt ctg ctc aac agt    96
Glu Arg Val Thr Met Asn Cys Lys Ser Ser Gln Ser Leu Leu Asn Ser
            20                  25                  30 gga atg cga aag agt ttc ttg gct tgg tac cag cag aaa cca ggg cag   144
Gly Met Arg Lys Ser Phe Leu Ala Trp Tyr Gln Gln Lys Pro Gly Gln
        35                  40                  45 tct cct aag ctg ctg atc tac tgg gca tcc act agg gaa tct ggg gtc   192
Ser Pro Lys Leu Leu Ile Tyr Trp Ala Ser Thr Arg Glu Ser Gly Val
    50                  55                  60 cct gat cgc ttc aca ggc agt gga tct ggg aca gat ttc act ctc acc   240
Pro Asp Arg Phe Thr Gly Ser Gly Ser Gly Thr Asp Phe Thr Leu Thr
65                  70                  75                  80 atc agc agt gtg cag gct gaa gac gtc gca gtt tat tac tgc aag caa   288
Ile Ser Ser Val Gln Ala Glu Asp Val Ala Val Tyr Tyr Cys Lys Gln
                85                  90                  95 tct tat cat cta ttc acg ttc ggc tcg ggg aca aag ttg gaa ata aaa   336
Ser Tyr His Leu Phe Thr Phe Gly Ser Gly Thr Lys Leu Glu Ile Lys
                100                 105                 110
```

<210> SEQ ID NO 8
<211> LENGTH: 112
<212> TYPE: PRT
<213> ORGANISM: Artificial sequence
<220> FEATURE:
<223> OTHER INFORMATION: Synthetic Construct

<400> SEQUENCE: 8

Asp Ile Val Leu Thr Gln Ser Pro Asp Ser Leu Ala Val Ser Leu Gly

-continued

```
            1               5                  10                 15
Glu Arg Val Thr Met Asn Cys Lys Ser Ser Gln Ser Leu Leu Asn Ser
                20                  25                  30

Gly Met Arg Lys Ser Phe Leu Ala Trp Tyr Gln Gln Lys Pro Gly Gln
                35                  40                  45

Ser Pro Lys Leu Leu Ile Tyr Trp Ala Ser Thr Arg Glu Ser Gly Val
                50                  55                  60

Pro Asp Arg Phe Thr Gly Ser Gly Ser Gly Thr Asp Phe Thr Leu Thr
 65             70                  75                  80

Ile Ser Ser Val Gln Ala Glu Asp Val Ala Val Tyr Tyr Cys Lys Gln
                85                  90                  95

Ser Tyr His Leu Phe Thr Phe Gly Ser Gly Thr Lys Leu Glu Ile Lys
                100                 105                 110
```

<210> SEQ ID NO 9
<211> LENGTH: 24
<212> TYPE: DNA
<213> ORGANISM: Artificial sequence
<220> FEATURE:
<223> OTHER INFORMATION: Oligonucleotide primer

<400> SEQUENCE: 9
atggratgga gctgkatcwt thtc                                    24

<210> SEQ ID NO 10
<211> LENGTH: 25
<212> TYPE: DNA
<213> ORGANISM: Artificial sequence
<220> FEATURE:
<223> OTHER INFORMATION: Oligonucleotide primer

<400> SEQUENCE: 10
casaymcagg ggccagtgga tagac                                   25

<210> SEQ ID NO 11
<211> LENGTH: 27
<212> TYPE: DNA
<213> ORGANISM: Artificial sequence
<220> FEATURE:
<223> OTHER INFORMATION: Oligonucleotide primer

<400> SEQUENCE: 11
atgragtcac akacycaggt cttyrta                                 27

<210> SEQ ID NO 12
<211> LENGTH: 24
<212> TYPE: DNA
<213> ORGANISM: Artificial sequence
<220> FEATURE:
<223> OTHER INFORMATION: Oligonucleotide primer

<400> SEQUENCE: 12
gctcactgga tggtgggaag atgg                                    24

<210> SEQ ID NO 13
<211> LENGTH: 31
<212> TYPE: DNA
<213> ORGANISM: Artificial sequence
<220> FEATURE:
<223> OTHER INFORMATION: Oligonucleotide primer

<400> SEQUENCE: 13
ccaccggtga cattgtgctg acccagtctc c                            31

<210> SEQ ID NO 14
<211> LENGTH: 34
<212> TYPE: DNA
<213> ORGANISM: Artificial sequence
<220> FEATURE:
<223> OTHER INFORMATION: Oligonucleotide primer

<400> SEQUENCE: 14
caccgtacgt tttatttcca actttgtccc cgag                              34

<210> SEQ ID NO 15
<211> LENGTH: 22
<212> TYPE: DNA
<213> ORGANISM: Artificial sequence
<220> FEATURE:
<223> OTHER INFORMATION: Oligonucleotide primer

<400> SEQUENCE: 15
caggtccagc tgcagcagtc tg                                          22

<210> SEQ ID NO 16
<211> LENGTH: 40
<212> TYPE: DNA
<213> ORGANISM: Artificial sequence
<220> FEATURE:
<223> OTHER INFORMATION: Oligonucleotide primer

<400> SEQUENCE: 16
gatgggccct tggtcgacgc tgaggagact gtgagcaggg                        40

<210> SEQ ID NO 17
<211> LENGTH: 8
<212> TYPE: PRT
<213> ORGANISM: Mus musculus
<220> FEATURE:
<221> NAME/KEY: MISC_FEATURE
<222> LOCATION: (1)..(8)
<223> OTHER INFORMATION: CDR1 heavy chain 16D3

<400> SEQUENCE: 17

Gly Tyr Thr Phe Thr Asp Tyr Tyr
1               5

<210> SEQ ID NO 18
<211> LENGTH: 8
<212> TYPE: PRT
<213> ORGANISM: Mus musculus
<220> FEATURE:
<221> NAME/KEY: MISC_FEATURE
<222> LOCATION: (1)..(8)
<223> OTHER INFORMATION: CDR2 heavy chain 16D3

<400> SEQUENCE: 18

Ile Tyr Pro Gly Ser Gly Asn Thr
1               5

<210> SEQ ID NO 19
<211> LENGTH: 9
<212> TYPE: PRT
<213> ORGANISM: Mus musculus
<220> FEATURE:
<221> NAME/KEY: MISC_FEATURE
<222> LOCATION: (1)..(9)
<223> OTHER INFORMATION: CDR3 heavy chain 16D3

<400> SEQUENCE: 19

-continued

Val Arg Asp Ser Pro Phe Phe Asp Tyr
1               5

<210> SEQ ID NO 20
<211> LENGTH: 12
<212> TYPE: PRT
<213> ORGANISM: Mus musculus
<220> FEATURE:
<221> NAME/KEY: MISC_FEATURE
<222> LOCATION: (1)..(12)
<223> OTHER INFORMATION: CDR1 light chain 16D3

<400> SEQUENCE: 20

Gln Ser Leu Leu Asn Ser Gly Met Arg Lys Ser Phe
1               5                   10

<210> SEQ ID NO 21
<211> LENGTH: 3
<212> TYPE: PRT
<213> ORGANISM: Mus musculus
<220> FEATURE:
<221> NAME/KEY: MISC_FEATURE
<222> LOCATION: (1)..(3)
<223> OTHER INFORMATION: CDR2 light chain 16D3

<400> SEQUENCE: 21

Trp Ala Ser
1

<210> SEQ ID NO 22
<211> LENGTH: 8
<212> TYPE: PRT
<213> ORGANISM: Mus musculus
<220> FEATURE:
<221> NAME/KEY: MISC_FEATURE
<222> LOCATION: (1)..(8)
<223> OTHER INFORMATION: CDR3 light chain 16D3

<400> SEQUENCE: 22

Lys Gln Ser Tyr His Leu Phe Thr
1               5

<210> SEQ ID NO 23
<211> LENGTH: 786
<212> TYPE: DNA
<213> ORGANISM: Artificial sequence
<220> FEATURE:
<223> OTHER INFORMATION: 16D3 ScFv
<220> FEATURE:
<221> NAME/KEY: CDS
<222> LOCATION: (1)..(786)
<220> FEATURE:
<221> NAME/KEY: misc_feature
<222> LOCATION: (1)..(348)
<223> OTHER INFORMATION: Heavy chain
<220> FEATURE:
<221> NAME/KEY: misc_feature
<222> LOCATION: (349)..(393)
<223> OTHER INFORMATION: Linker
<220> FEATURE:
<221> NAME/KEY: misc_feature
<222> LOCATION: (394)..(729)
<223> OTHER INFORMATION: Light chain
<220> FEATURE:
<221> NAME/KEY: misc_feature
<222> LOCATION: (736)..(762)
<223> OTHER INFORMATION: HA-Tag
<220> FEATURE:
<221> NAME/KEY: misc_feature
<222> LOCATION: (769)..(786)
<223> OTHER INFORMATION: His-Tag

<400> SEQUENCE: 23

```
cag atc cag ctg cag cag tct gga cct gag ctg gtg aag cct ggg gct      48
Gln Ile Gln Leu Gln Gln Ser Gly Pro Glu Leu Val Lys Pro Gly Ala
1               5                   10                  15 tca gtg aag ata tcc tgc aag gcc tct ggc tac acc ttc act gac tac      96
Ser Val Lys Ile Ser Cys Lys Ala Ser Gly Tyr Thr Phe Thr Asp Tyr
            20                  25                  30 tat ata aac tgg gtg aag ttg aag cct gga cag gga ctt gag tgg att     144
Tyr Ile Asn Trp Val Lys Leu Lys Pro Gly Gln Gly Leu Glu Trp Ile
        35                  40                  45 gga tgg att tat cct gga agc ggt aat act aag tac aat gag aag ttc     192
Gly Trp Ile Tyr Pro Gly Ser Gly Asn Thr Lys Tyr Asn Glu Lys Phe
    50                  55                  60 aag ggc aag gcc aca ttg act ata gac aca tcc tcc agc aca gcc tac     240
Lys Gly Lys Ala Thr Leu Thr Ile Asp Thr Ser Ser Ser Thr Ala Tyr
65                  70                  75                  80 atg cag ctc agc agc ctg aca tct gag gac act gct gtc tat ttc tgt     288
Met Gln Leu Ser Ser Leu Thr Ser Glu Asp Thr Ala Val Tyr Phe Cys
                85                  90                  95 gta aga gac agc cct ttc ttt gac tac tgg ggc caa ggc acc act ctc     336
Val Arg Asp Ser Pro Phe Phe Asp Tyr Trp Gly Gln Gly Thr Thr Leu
            100                 105                 110 aca gtc tcc tca ggt ggt ggt ggt tct ggc ggc ggc ggc tcc ggt gga     384
Thr Val Ser Ser Gly Gly Gly Gly Ser Gly Gly Gly Gly Ser Gly Gly
        115                 120                 125 ggt ggt tct gac att gtg ctg tca cag tct cca tcc tcc ctg gct gtg     432
Gly Gly Ser Asp Ile Val Leu Ser Gln Ser Pro Ser Ser Leu Ala Val
    130                 135                 140 tca gca gga gag aag gtc act atg cgc tgc aaa tcc agt cag agt ctg     480
Ser Ala Gly Glu Lys Val Thr Met Arg Cys Lys Ser Ser Gln Ser Leu
145                 150                 155                 160 ctc aac agt gga atg cga aag agt ttc ttg gct tgg tac cag cag aaa     528
Leu Asn Ser Gly Met Arg Lys Ser Phe Leu Ala Trp Tyr Gln Gln Lys
                165                 170                 175 cca ggg cag tct cct aag ctg ctg atc tac tgg gca tcc act agg gaa     576
Pro Gly Gln Ser Pro Lys Leu Leu Ile Tyr Trp Ala Ser Thr Arg Glu
            180                 185                 190 tct ggg gtc cct gat cgc ttc aca ggc agt gga tct ggg aca gat ttc     624
Ser Gly Val Pro Asp Arg Phe Thr Gly Ser Gly Ser Gly Thr Asp Phe
        195                 200                 205 act ctc acc atc agc agt gtg cag gct gaa gac ctg gca gtt tat tac     672
Thr Leu Thr Ile Ser Ser Val Gln Ala Glu Asp Leu Ala Val Tyr Tyr
    210                 215                 220 tgc aag caa tct tat cat cta ttc acg ttc ggc tcg ggg aca aag ttg     720
Cys Lys Gln Ser Tyr His Leu Phe Thr Phe Gly Ser Gly Thr Lys Leu
225                 230                 235                 240 gaa ata aaa ggt tct tac cca tac gac gtc cca gac tac gct ggt tct     768
Glu Ile Lys Gly Ser Tyr Pro Tyr Asp Val Pro Asp Tyr Ala Gly Ser
                245                 250                 255 cat cac cac cat cac cat                                              786
His His His His His His
                260
```

<210> SEQ ID NO 24
<211> LENGTH: 262
<212> TYPE: PRT
<213> ORGANISM: Artificial sequence
<220> FEATURE:
<223> OTHER INFORMATION: Synthetic Construct

<400> SEQUENCE: 24

```
Gln Ile Gln Leu Gln Gln Ser Gly Pro Glu Leu Val Lys Pro Gly Ala
  1               5                  10                  15

Ser Val Lys Ile Ser Cys Lys Ala Ser Gly Tyr Thr Phe Thr Asp Tyr
             20                  25                  30

Tyr Ile Asn Trp Val Lys Leu Lys Pro Gly Gln Gly Leu Glu Trp Ile
         35                  40                  45

Gly Trp Ile Tyr Pro Gly Ser Gly Asn Thr Lys Tyr Asn Glu Lys Phe
 50                  55                  60

Lys Gly Lys Ala Thr Leu Thr Ile Asp Thr Ser Ser Ser Thr Ala Tyr
 65                  70                  75                  80

Met Gln Leu Ser Ser Leu Thr Ser Glu Asp Thr Ala Val Tyr Phe Cys
                 85                  90                  95

Val Arg Asp Ser Pro Phe Phe Asp Tyr Trp Gly Gln Gly Thr Thr Leu
            100                 105                 110

Thr Val Ser Ser Gly Gly Gly Ser Gly Gly Gly Gly Ser Gly Gly
            115                 120                 125

Gly Gly Ser Asp Ile Val Leu Ser Gln Ser Pro Ser Ser Leu Ala Val
130                 135                 140

Ser Ala Gly Glu Lys Val Thr Met Arg Cys Lys Ser Gln Ser Leu
145                 150                 155             160

Leu Asn Ser Gly Met Arg Lys Ser Phe Leu Ala Trp Tyr Gln Gln Lys
                165                 170                 175

Pro Gly Gln Ser Pro Lys Leu Leu Ile Tyr Trp Ala Ser Thr Arg Glu
            180                 185                 190

Ser Gly Val Pro Asp Arg Phe Thr Gly Ser Gly Ser Gly Thr Asp Phe
            195                 200                 205

Thr Leu Thr Ile Ser Ser Val Gln Ala Glu Asp Leu Ala Val Tyr Tyr
            210                 215                 220

Cys Lys Gln Ser Tyr His Leu Phe Thr Phe Gly Ser Gly Thr Lys Leu
225                 230                 235                 240

Glu Ile Lys Gly Ser Tyr Pro Tyr Asp Val Pro Asp Tyr Ala Gly Ser
                245                 250                 255

His His His His His His
            260
```

```
<210> SEQ ID NO 25
<211> LENGTH: 786
<212> TYPE: DNA
<213> ORGANISM: Artificial sequence
<220> FEATURE:
<223> OTHER INFORMATION: 16D3 ScFv Humanised
<220> FEATURE:
<221> NAME/KEY: CDS
<222> LOCATION: (1)..(786)
<220> FEATURE:
<221> NAME/KEY: misc_feature
<222> LOCATION: (1)..(348)
<223> OTHER INFORMATION: Heavy chain
<220> FEATURE:
<221> NAME/KEY: misc_feature
<222> LOCATION: (349)..(393)
<223> OTHER INFORMATION: linker
<220> FEATURE:
<221> NAME/KEY: misc_feature
<222> LOCATION: (394)..(729)
<223> OTHER INFORMATION: Light chain
<220> FEATURE:
<221> NAME/KEY: misc_feature
<222> LOCATION: (736)..(762)
<223> OTHER INFORMATION: HA-Tag
<220> FEATURE:
```

<221> NAME/KEY: misc_feature
<222> LOCATION: (769)..(786)
<223> OTHER INFORMATION: HA-Tag

<400> SEQUENCE: 25

| | | | | | | | | | | | | | | | | |
|---|---|---|---|---|---|---|---|---|---|---|---|---|---|---|---|---|
| cag | gtc | cag | ctg | cag | cag | tct | gga | gcc | gag | ctg | gtg | aag | cct | ggg | gct | 48 |
| Gln | Val | Gln | Leu | Gln | Gln | Ser | Gly | Ala | Glu | Leu | Val | Lys | Pro | Gly | Ala | |
| 1 | | | | 5 | | | | | 10 | | | | | 15 | | |
| tca | gtg | aag | ata | tcc | tgc | aag | gcc | tct | ggc | tac | acc | ttc | act | gac | tac | 96 |
| Ser | Val | Lys | Ile | Ser | Cys | Lys | Ala | Ser | Gly | Tyr | Thr | Phe | Thr | Asp | Tyr | |
| | | | 20 | | | | | 25 | | | | | 30 | | | |
| tat | ata | aac | tgg | gtg | aag | ttg | gcc | cct | gga | cag | gga | ctt | gag | tgg | att | 144 |
| Tyr | Ile | Asn | Trp | Val | Lys | Leu | Ala | Pro | Gly | Gln | Gly | Leu | Glu | Trp | Ile | |
| | | 35 | | | | | 40 | | | | | 45 | | | | |
| gga | tgg | att | tat | cct | gga | agc | ggt | aat | act | aag | tac | aat | gag | aag | ttc | 192 |
| Gly | Trp | Ile | Tyr | Pro | Gly | Ser | Gly | Asn | Thr | Lys | Tyr | Asn | Glu | Lys | Phe | |
| | 50 | | | | | 55 | | | | | 60 | | | | | |
| aag | ggc | aag | gcc | aca | ttg | act | ata | gac | aca | tcc | tcc | agc | aca | gcc | tac | 240 |
| Lys | Gly | Lys | Ala | Thr | Leu | Thr | Ile | Asp | Thr | Ser | Ser | Ser | Thr | Ala | Tyr | |
| 65 | | | | | 70 | | | | | 75 | | | | | 80 | |
| atg | cag | ctc | agc | agc | ctg | aca | tct | gag | gac | act | gct | gtc | tat | ttc | tgt | 288 |
| Met | Gln | Leu | Ser | Ser | Leu | Thr | Ser | Glu | Asp | Thr | Ala | Val | Tyr | Phe | Cys | |
| | | | | 85 | | | | | 90 | | | | | 95 | | |
| gta | aga | gac | agc | cct | ttc | ttt | gac | tac | tgg | ggc | caa | ggc | acc | ctg | ctc | 336 |
| Val | Arg | Asp | Ser | Pro | Phe | Phe | Asp | Tyr | Trp | Gly | Gln | Gly | Thr | Leu | Leu | |
| | | | 100 | | | | | 105 | | | | | 110 | | | |
| aca | gtc | tcc | tca | ggt | ggt | ggt | ggt | tct | ggc | ggc | ggc | ggc | tcc | ggt | gga | 384 |
| Thr | Val | Ser | Ser | Gly | Gly | Gly | Gly | Ser | Gly | Gly | Gly | Gly | Ser | Gly | Gly | |
| | | 115 | | | | | 120 | | | | | 125 | | | | |
| ggt | ggt | tct | gac | att | gtg | ctg | acc | cag | tct | cca | gac | tcc | ctg | gct | gtg | 432 |
| Gly | Gly | Ser | Asp | Ile | Val | Leu | Thr | Gln | Ser | Pro | Asp | Ser | Leu | Ala | Val | |
| | 130 | | | | | 135 | | | | | 140 | | | | | |
| tca | ctg | gga | gag | cgg | gtc | act | atg | aac | tgc | aaa | tcc | agt | cag | agt | ctg | 480 |
| Ser | Leu | Gly | Glu | Arg | Val | Thr | Met | Asn | Cys | Lys | Ser | Ser | Gln | Ser | Leu | |
| 145 | | | | | 150 | | | | | 155 | | | | | 160 | |
| ctc | aac | agt | gga | atg | cga | aag | agt | ttc | ttg | gct | tgg | tac | cag | cag | aaa | 528 |
| Leu | Asn | Ser | Gly | Met | Arg | Lys | Ser | Phe | Leu | Ala | Trp | Tyr | Gln | Gln | Lys | |
| | | | | 165 | | | | | 170 | | | | | 175 | | |
| cca | ggg | cag | tct | cct | aag | ctg | ctg | atc | tac | tgg | gca | tcc | act | agg | gaa | 576 |
| Pro | Gly | Gln | Ser | Pro | Lys | Leu | Leu | Ile | Tyr | Trp | Ala | Ser | Thr | Arg | Glu | |
| | | | 180 | | | | | 185 | | | | | 190 | | | |
| tct | ggg | gtc | cct | gat | cgc | ttc | aca | ggc | agt | gga | tct | ggg | aca | gat | ttc | 624 |
| Ser | Gly | Val | Pro | Asp | Arg | Phe | Thr | Gly | Ser | Gly | Ser | Gly | Thr | Asp | Phe | |
| | | 195 | | | | | 200 | | | | | 205 | | | | |
| act | ctc | acc | atc | agc | agt | gtg | cag | gct | gaa | gac | gtc | gca | gtt | tat | tac | 672 |
| Thr | Leu | Thr | Ile | Ser | Ser | Val | Gln | Ala | Glu | Asp | Val | Ala | Val | Tyr | Tyr | |
| | 210 | | | | | 215 | | | | | 220 | | | | | |
| tgc | aag | caa | tct | tat | cat | cta | ttc | acg | ttc | ggc | tcg | ggg | aca | aag | ttg | 720 |
| Cys | Lys | Gln | Ser | Tyr | His | Leu | Phe | Thr | Phe | Gly | Ser | Gly | Thr | Lys | Leu | |
| 225 | | | | | 230 | | | | | 235 | | | | | 240 | |
| gaa | ata | aaa | ggt | tct | tac | cca | tac | gac | gtc | cca | gac | tac | gct | ggt | tct | 768 |
| Glu | Ile | Lys | Gly | Ser | Tyr | Pro | Tyr | Asp | Val | Pro | Asp | Tyr | Ala | Gly | Ser | |
| | | | | 245 | | | | | 250 | | | | | 255 | | |
| cat | cat | cac | cat | cac | cat | | | | | | | | | | | 786 |
| His | His | His | His | His | His | | | | | | | | | | | |
| | | | 260 | | | | | | | | | | | | | |

<210> SEQ ID NO 26
<211> LENGTH: 262
<212> TYPE: PRT
<213> ORGANISM: Artificial sequence
<220> FEATURE:
<223> OTHER INFORMATION: Synthetic Construct

<400> SEQUENCE: 26

| | | | | | | | | | | | | | | |
|---|---|---|---|---|---|---|---|---|---|---|---|---|---|---|
| Gln | Val | Gln | Leu | Gln | Gln | Ser | Gly | Ala | Glu | Leu | Val | Lys | Pro | Gly | Ala |
| 1 | | | | 5 | | | | | 10 | | | | | 15 | |
| Ser | Val | Lys | Ile | Ser | Cys | Lys | Ala | Ser | Gly | Tyr | Thr | Phe | Thr | Asp | Tyr |
| | | | 20 | | | | | 25 | | | | | 30 | | |
| Tyr | Ile | Asn | Trp | Val | Lys | Leu | Ala | Pro | Gly | Gln | Gly | Leu | Glu | Trp | Ile |
| | | | 35 | | | | | 40 | | | | | 45 | | |
| Gly | Trp | Ile | Tyr | Pro | Gly | Ser | Gly | Asn | Thr | Lys | Tyr | Asn | Glu | Lys | Phe |
| | 50 | | | | | 55 | | | | | 60 | | | | |
| Lys | Gly | Lys | Ala | Thr | Leu | Thr | Ile | Asp | Thr | Ser | Ser | Thr | Ala | Tyr |
| 65 | | | | | 70 | | | | | 75 | | | | | 80 |
| Met | Gln | Leu | Ser | Ser | Leu | Thr | Ser | Glu | Asp | Thr | Ala | Val | Tyr | Phe | Cys |
| | | | | 85 | | | | | 90 | | | | | 95 | |
| Val | Arg | Asp | Ser | Pro | Phe | Phe | Asp | Tyr | Trp | Gly | Gln | Gly | Thr | Leu | Leu |
| | | | 100 | | | | | 105 | | | | | 110 | | |
| Thr | Val | Ser | Ser | Gly | Gly | Gly | Gly | Ser | Gly | Gly | Gly | Gly | Ser | Gly | Gly |
| | | 115 | | | | | 120 | | | | | 125 | | | |
| Gly | Gly | Ser | Asp | Ile | Val | Leu | Thr | Gln | Ser | Pro | Asp | Ser | Leu | Ala | Val |
| 130 | | | | | 135 | | | | | 140 | | | | | |
| Ser | Leu | Gly | Glu | Arg | Val | Thr | Met | Asn | Cys | Lys | Ser | Gln | Ser | Leu |
| 145 | | | | | 150 | | | | | 155 | | | | | 160 |
| Leu | Asn | Ser | Gly | Met | Arg | Lys | Ser | Phe | Leu | Ala | Trp | Tyr | Gln | Gln | Lys |
| | | | | 165 | | | | | 170 | | | | | 175 | |
| Pro | Gly | Gln | Ser | Pro | Lys | Leu | Leu | Ile | Tyr | Trp | Ala | Ser | Thr | Arg | Glu |
| | | | 180 | | | | | 185 | | | | | 190 | | |
| Ser | Gly | Val | Pro | Asp | Arg | Phe | Thr | Gly | Ser | Gly | Ser | Gly | Thr | Asp | Phe |
| | | 195 | | | | | 200 | | | | | 205 | | | |
| Thr | Leu | Thr | Ile | Ser | Ser | Val | Gln | Ala | Glu | Asp | Val | Ala | Val | Tyr | Tyr |
| | 210 | | | | | 215 | | | | | 220 | | | | |
| Cys | Lys | Gln | Ser | Tyr | His | Leu | Phe | Thr | Phe | Gly | Ser | Gly | Thr | Lys | Leu |
| 225 | | | | | 230 | | | | | 235 | | | | | 240 |
| Glu | Ile | Lys | Gly | Ser | Tyr | Pro | Tyr | Asp | Val | Pro | Asp | Tyr | Ala | Gly | Ser |
| | | | | 245 | | | | | 250 | | | | | 255 | |
| His | His | His | His | His | His |
| | | | 260 | | |

<210> SEQ ID NO 27
<211> LENGTH: 22
<212> TYPE: DNA
<213> ORGANISM: Artificial sequence
<220> FEATURE:
<223> OTHER INFORMATION: Oligonucleotide primer

<400> SEQUENCE: 27
caggtccagc tgcagcagtc tg    22

<210> SEQ ID NO 28
<211> LENGTH: 40
<212> TYPE: DNA
<213> ORGANISM: Artificial sequence
<220> FEATURE:
<223> OTHER INFORMATION: Oligonucleotide primer

<400> SEQUENCE: 28
gatgggccct tggtcgacgc tgaggagact gtgagcaggg    40

```
<210> SEQ ID NO 29
<211> LENGTH: 31
<212> TYPE: DNA
<213> ORGANISM: Artificial sequence
<220> FEATURE:
<223> OTHER INFORMATION: Oligonucleotide primer

<400> SEQUENCE: 29
ccaccggtga cattgtgctg acccagtctc c                                  31

<210> SEQ ID NO 30
<211> LENGTH: 34
<212> TYPE: DNA
<213> ORGANISM: Artificial sequence
<220> FEATURE:
<223> OTHER INFORMATION: Oligonucleotide primer

<400> SEQUENCE: 30
caccgtacgt tttatttcca actttgtccc cgag                               34
```

ANTI-PLGF ANTIBODY

CROSS-REFERENCE TO RELATED APPLICATIONS

This application is the U.S. National Stage of International Application No. PCT/BE2006/000023, filed Mar. 24, 2006, which claims the benefit of U.S. Application No. 60/664,768, filed Mar. 24, 2005.

FIELD OF THE INVENTION

The present invention relates to novel antibodies and fragments and derivatives thereof particularly suited for the inhibition of angiogenesis in pathological conditions. The invention also relates to cell lines producing the specific antibodies. The present invention provides pharmaceutical compositions comprising the antibodies, fragments and/or derivatives of the invention and provides methods of preventing and treating angiogenesis and/or vascular leakage where these are undesired such as in tumour formation, diseases of the eye, pulmonary hypertension and inflammatory disorders and methods of preventing and treating bone disorders such as osteoporosis.

BACKGROUND OF THE INVENTION

Abnormal blood vessel formation contributes to the pathogenesis of numerous diseases with high morbidity and mortality. Elucidation of the mechanisms underlying vascular growth might allow the development of therapeutic strategies to stimulate vascular growth in ischemic tissues or to suppress their formation in tumours. Recent gene targeting studies in embryos have identified some of the mechanisms involved in the initial formation of endothelial channels (angiogenesis) and their subsequent maturation by coverage with smooth muscle cells (arteriogenesis). Evidence is emerging that distinct molecular mechanisms may mediate growth of blood vessels during pathological conditions, but the molecular players remain largely undetermined.

It has been established that Vascular Endothelial Growth Factor (VEGF) is implicated in development and pathological growth of the vasculature (Ferrara N. et al, 1999, Curr Top Microbiol Immunol 237, 1-30). Furthermore, it has also been shown that Placental growth factor (PlGF), a homologue of VEGF, is a specific modulator of VEGF during a variety of pathological conditions, such as ischemic retinopathy, tumourigenesis, inflammatory disorders, and oedema. It has been shown that PlGF$^{-/-}$ mice have an impaired angiogenesis and arteriogenesis in disease (Carmeliet P. et al., 2000, J. Pathol. 190, 387-405), while the physiological angiogenesis in normal health remains unaffected. Thus inhibitors of PlGF have a huge potential for the treatment of diseases in which angiogenesis or arteriogenesis contribute to the pathogenicity of the disease.

Inhibitors for PlGF are known in the art, such as a goat polyclonal antibody against human PlGF (R&D pharmaceuticals, Abingdon, UK) and a chicken polyclonal antibody (Gassmann et al., 1990, Faseb J. 4, 2528). Those antibodies are used for Western blotting, histochemistry and immunoprecipitation studies. WO01/85796 describes the use of inhibitors of PlGF, including monoclonal anti-PlGF antibodies, for the treatment or prevention of diseases, such as tumour formation. More specifically, the preparation of murine monoclonal antibodies which fully inhibit murine PlGF-2 binding to its receptor Flt-1, is described, whereby the antibody Mab-PL5D11, is selected as having the most efficient inhibitory activity. Use of the antibody in animal models of pathological angiogenesis is described.

Antibodies generated in animals have characteristics which may severely limit their use in human therapy. As foreign proteins, they may elicit an anti-immunoglobulin response (which for mouse antibodies is referred to as human anti-mouse antibody or HAMA) that reduces or destroys their therapeutic efficacy and/or provokes allergic or hypersensitivity reactions in patients, as taught by Jaffers et al., 1986 (Transplantation 1986 41:572). While the use of human monoclonal antibodies would address this limitation, it has proven difficult to generate large amounts of human antihuman antibodies by conventional hybridoma technology. Recombinant technology has therefore been used in the art to construct "humanized" antibodies that maintain the high binding affinity of animal, such as murine monoclonal antibodies but exhibit reduced immunogenicity in humans. In particular, chimeric antibodies have been suggested in which the variable region (V) of a non-human antibody is combined with the constant (C) region of a human antibody. Methods of obtaining such chimerical immunoglobulins are described in detail in U.S. Pat. No. 5,770,198. In other attempts to reduce the immunogenicity of murine antibodies, only the complementarity determining region (CDR), i.e. regions of hypervariability in the V regions, rather than the entire V domain, are transplanted to a human antibody. Such humanized antibodies are known as CDR-grafted antibodies. The construction of CDR-grafted antibodies recognizing more complex antigens has resulted in antibodies having binding activity significantly lower than the native non-humanized antibodies. In numerous cases it was demonstrated that the mere introduction of non-human CDRs into a human antibody backbone is insufficient to maintain full binding activity. While a refined computer model of the murine antibody of interest is required in order to identify critical amino-acids to be considered in the design of a humanized antibody, and general theoretical guidelines were proposed for such design, in all cases the procedure must be tailored and optimized for the particular non-human antibody of interest.

Subsequently, there remains a need for (monoclonal) antibodies which optimally inhibit human PlGF binding to its receptor. Furthermore, such antibodies also need to be non-immunogenic, in that they can not elicit HAMA (or have a low tendency to do so).

SUMMARY OF THE INVENTION

The present invention relates to novel monoclonal antibodies and derivatives thereof directed to PlGF and capable of inhibiting the binding of PlGF to its receptor. The present ligands are the first to demonstrate inhibition of human PlGF in a pathological condition in vivo. More specifically, the antibodies and derivatives thereof according to the present invention are capable of reducing tumor size and vascularization of human tumor tissue in Vivo. The antibodies of the present invention provide an alternative to anti-angiogenic therapies targeting VEGF currently used, with the important advantage that the side-effects caused by inhibition of physiological angiogenesis associated with these therapies is significantly reduced.

The present invention relates to antigen-binding molecules, particularly monoclonal antibodies, fragments or derivatives thereof, including humanized antibodies and antibody fragments, which bind to the same epitope of PlGF as the antibody referred to herein as 16D3.

A first object of the present invention is the provision of novel monoclonal antibodies capable of binding to PlGF and having the capacity to inhibit the functioning of PlGF, more specifically antibodies characterized in that their heavy chain variable region comprises the sequence of SEQ ID NO: 2 or a sequence having at least 80%, more particularly at least 90%, most particularly 95% sequence identity therewith in the CDR regions and/or in that their light chain variable region comprises the sequence of SEQ ID NO: 4 or a sequence having at least 80%, particularly at least 85%, more particularly at least 90%, most particularly at least 95% sequence identity therewith in the CDR regions, such as antibody 16D3 or derivatives thereof. Additionally or alternatively, in a further embodiment, the antigen-binding molecules of the present invention have a sequence identity within the heavy and/or light chain variable regions outside the CDR regions which is at least 70%, particularly at least 80%, more particularly at least 90%, most particularly at least 95% identical with the sequences of SEQ ID NO: 2 and SEQ ID NO: 4, respectively.

According to a particular embodiment of the invention, the antibody is a humanized antibody, more particularly a hybrid antibody, most particularly a mouse/human hybrid antibody, more particularly a hybrid mouse 16D3/human IgG1κ or IgG4κ. Alternatively the humanized antibody is one which comprises the CDR regions of the mouse 16D3 antibody of the present invention capable of binding to PlGF, grafted onto the backbone of a human antibody.

A further embodiment of the present invention relates to antigen-binding fragments of the mouse 16D3 antibody or a derivative thereof, such as a humanized antibody thereof, such as but not limited to an Fab, Fab' or F(ab')$_2$, a combination of at least two complementarity determining regions (CDRs), a soluble or membrane-anchored single-chain variable region, or single variable domain. Particular embodiments of such antigen-binding fragments include fragments which comprise at least two CDRs of 16D3 or derivatives thereof or more particularly at least two CDRs selected from the group consisting of SEQ ID NO: 17 (GYTFTDYY), SEQ ID NO: 18 (IYPGSGNT); SEQ ID NO:19 (VRDSPFFDY), SEQ ID NO: 20 (QSLLNSGMRKSF), SEQ ID NO: 21 (WAS) and SEQ ID NO: 22 (KQSYHLFT), or which comprise at least two sequences having at least 80%, particularly at least 85%, more particularly at least 90%, most particularly at least 95% sequence identity therewith. A particular embodiment of the invention relates to the provision of single-chain variable fragments (scFvs) of the mouse 16D3 antibody and humanized scFvs which are capable of inhibiting PlGF activity. Most particularly the present invention provides scFvs comprising the amino acid sequence of SEQ ID NO:24 or SEQ ID NO: 26 or a sequence having at least 80%, particularly at least 85%, more particularly at least 90%, most particularly at least 95% sequence identity thereto within the CDRs capable of binding PlGF.

Yet a further object of the present invention is the provision of cell lines producing the monoclonal antibodies of the present invention, more particularly cell line 16D3 which produces the 16D3 antibody, but also other cell lines which are capable of producing the antigen-binding molecules derived from 16D3 or fragments thereof, for instance as a result of recombinant technology.

Yet a further object of the present invention is the provision of a pharmaceutical composition for the prevention or treatment of (undesired) angiogenesis in pathological conditions or disorders in mammals or for the prevention or treatment of bone resorption, which comprises an antibody against PlGF which is 16D3 or a fragment or derivative, more particularly a humanized version of 16D3 or an antigen-binding fragment thereof in admixture with a pharmaceutically acceptable carrier. A specific embodiment of the invention is a pharmaceutical composition which comprises an antigen-binding fragment of 16D3 or a derivative thereof, which is selected from the group consisting of an Fab, Fab' or F(ab')$_2$, a soluble or membrane-anchored single-chain variable part or a single variable domain. Most particular embodiments of the present invention relate to pharmaceutical compositions comprising an antigen-binding fragment which comprises at least two CDRs selected from the group consisting of SEQ ID NO: 17 (GYTFTDYY), SEQ ID NO: 18 (IYPGSGNT); SEQ ID NO:19 (VRDSPFFDY), SEQ ID NO: 20 (QSLLNSGMRKSF), SEQ ID NO: 21 (WAS) and SEQ ID NO: 22 (KQSYHLFT), or at least two having at least 80%, particularly at least 85%, more particularly at least 90%, most particularly at least 95% sequence identity with two different sequences selected from the group consisting of SEQ ID NO: 17 to 22. A particular embodiment of thereof relates to pharmaceutical compositions comprising a scFv of the 16D3 antibody of the invention, more particularly comprising a scFV comprising at least two CDRs selected from the group consisting of SEQ ID NO: 17 (GYTFTDYY), SEQ ID NO: 18 (IYPGSGNT); SEQ ID NO:19 (VRDSPFFDY), SEQ ID NO: 20 (QSLLNSGMRKSF), SEQ ID NO: 21 (WAS) and SEQ ID NO: 22 (KQSYHLFT) or at least two sequences having at least 80%, particularly at least 85%, more particularly at least 90%, most particularly at least 95% sequence identity with two different sequences selected from the group consisting of SEQ ID NO: 17 to 22, such as a scFv comprising SEQ ID NO:24. Most particularly the pharmaceutical composition comprises a humanized scFv of 16D3, such as, but not limited to the humanized scFv comprising SEQ ID NO:26 or a sequence having at least 80%, particularly at least 85%, more particularly at least 90%, most particularly at least 95% sequence identity therewith in the CDRs capable of binding PlGF.

In yet another particular embodiment of the pharmaceutical composition according to the invention, a therapeutically effective amount of another anti-angiogenic agent is included in addition to the antigen-binding molecule capable of binding to PlGF of the invention. Most particularly in this respect anti-angiogenic agents such as VEGF- and bFGF-inhibitors are envisaged, most particularly anti-VEGF antibodies.

Another object of the present invention is to provide nucleotide sequences encoding the antigen-binding fragments of the antibodies binding to PlGF disclosed herein, more particularly nucleotide sequences encoding the heavy and light chain variable regions of 16D3 produced by cell line 16D3. Most specifically the nucleotide sequence encoding the variable regions of SEQ ID NO: 2 and SEQ ID NO: 4 are envisaged. Additionally polynucleotide sequences encoding antigen-binding fragments comprising at least two CDRs of 16D3, more specifically, polynucleotides encoding at least two of the CDRs selected from the group consisting of SEQ ID NO: 17 (GYTFTDYY), SEQ ID NO: 18 (IYPGSGNT); SEQ ID NO:19 (VRDSPFFDY), SEQ ID NO: 20 (QSLLNSGMRKSF), SEQ ID NO: 21 (WAS) and SEQ ID NO: 22 (KQSYHLFT), or encoding sequences comprising at least two CDRs having at least 80%, particularly at least 85%, more particularly at least 90%, most particularly at least 95% sequence identity with SEQ ID NO: 17 to 22. Specific embodiments of the nucleotide sequences of the present invention are provided in SEQ ID Nos 1, 3, 5 and 6. Further specific embodiments include the nucleotide sequences encoding the scFv of 16D3 and humanized versions thereof, most particularly the sequence of SEQ ID NO: 23 and SEQ ID NO: 25 and sequences having at least 80%, particularly at least 85%, more particularly at least 90%, most particularly at least 95% sequence identity therewith, most particularly within the regions encoding the CDR regions of the scFv. It will be appreciated however that a multitude of nucleotide sequences exist which fall under the scope of the present invention as a result of the redundancy in the genetic code.

Another object of the present invention is to provide a method of treatment and/or prevention of undesired (or pathological) angiogenesis in pathological condition in a mammal, which method comprises administering to a mammal in need of such treatment or prevention a therapeutically effective amount of an active ingredient which is antibody 16D3 of the present invention or an antigen-binding fragment or derivative thereof, most particularly a scFv as described herein. Particularly suited for the methods of the present invention are the humanized antibodies and antibody fragments, such as scFvs of 16D3 or derivatives thereof. A particular embodiment of the method of the invention relates to the treatment and/or prevention of pathological conditions such as, but not limited to cancer, inflammation, diseases of the eye, pulmonary hypertension and vascular leakage. A particular aim of the present invention is to provide an effective and safe therapy (i.e. without side-effects) for pathological angiogenesis, more in particular for tumor growth, inflammation, diseases of the eye or vascular leakage, in mammals, more particularly in humans. Most particularly the method of the present invention is suitable for the treatment and/or prevention of solid tumors, more particularly for the treatment and/or prevention of colon cancer, breast cancer, pancreatic cancer and melanomas.

Further uses of the antibodies and antigen-binding fragments of the present invention relate to the immunological detection of PlGF in human samples, as labeled targeting moieties in diagnostic methods and for the screening of compounds with an additive effect to PlGF inhibition in the treatment of cancer.

The present invention is based on the surprising determination of new ligands, namely new murine and humanized monoclonal antibodies and fragments, derivatives and homologs thereof which inhibit PlGF very efficiently. Most particularly the present invention demonstrates ligands capable of reducing tumor growth, most particularly capable of reducing the size of a tumor between 20% and 50%.

BRIEF DESCRIPTION OF THE FIGURES

The following description, not intended to limit the invention to specific embodiments described therein, may be understood in conjunction with the accompanying Figures, incorporated herein by reference, in which:

FIG. 4: Monoclonal antibody 16D3 inhibits tumor growth in a subcutaneous human pancreatic DanG xenograft tumor model. Treatment of nu/nu mice with tumors of approximately 60 mm$^3$ with anti-tPA ('control IgG') (1C8; 50 mg/kg body weight; n=10), anti-hPlGF 16D3 ('anti-hPlGF') (50 mg/kg body weight; n=10), anti-mPlGF (PL5D11D4 (obtained as described in WO01/85796; 50 mg/kg body weight; n=10), a combination of anti-hPlGF 16D3 and an anti-mPlGF PL5D11D4 ('anti-hPlGF/anti-mPlGF') (each 25 mg/kg body weight; n=10) and 'vehicle' (n=10) in accordance with an embodiment of the present invention. (A) Tumor size (B) tumor weight 18 days after tumor inoculation.

FIG. 5: Monoclonal antibody 16D3 inhibits tumor growth in a subcutaneous human pancreatic DanG xenograft tumor model in a dose dependent manner. Treatment of nu/nu mice with tumors of approximately 60 mm$^3$ with anti-hP1GF 16D3 (50 mg/kg='1000 µg'/'C', 37.5 mg/kg='750 µg'/'D', 25 mg/kg='500 µg'/'E', 12.5 mg/kg='250 µg'/'F'; n=10 for each concentration), control IgG ('1C8'/'B'; 50 mg/kg) and 'vehicle'/'A' (n=10) in accordance with an embodiment of the present invention. A: evolution of mean tumor size after tumor cell inoculation; B: average mean tumor size at day 20.

FIG. 6: Monoclonal antibody 16D3 inhibits tumor growth in a subcutaneous human breast MDA-MB xenograft tumor model. Treatment of nu/nu mice with tumors of approximately 60 mm$^3$ with anti-hPlGF 16D3 (50 mg/kg body weight; n=10) or vehicle three times a week in accordance with an embodiment of the present invention. A: tumor weight and B: tumor volume as determined 32 days post inoculation.

FIG. 7: Monoclonal antibody 16D3 inhibits tumor growth in a subcutaneous human colon LOVO xenograft tumor model. Treatment of nu/nu mice with tumors of approximately 60 mm$^3$ with anti-hPlGF 16D3 (50 mg/kg body weight; n=10) or vehicle three times a week in accordance with an embodiment of the present invention. A: tumor weight and B: tumor volume as determined 30 days post inoculation.

FIG. 11: Nucleotide and amino acid sequences of variable parts of murine antibody 16D3 in accordance with an embodiment of the present invention. A. Nucleotide sequence encoding variable part of heavy chain; B. Nucleotide sequence encoding variable part of light chain; C. Amino acid sequence of variable part of heavy chain; D. Amino acid sequence of variable part of light chain. Nucleotides or amino acids which can be modified for humanization purposes according to one embodiment of the invention are underlined.

FIG. 12: Nucleotide and amino acid sequences of humanized variable parts of 16D3 in accordance with an embodiment of the present invention. A. Nucleotide sequence encoding humanized variable part of heavy chain; B. Nucleotide sequence encoding humanized variable part of light chain; C. Amino acid sequence of humanized variable part of heavy chain; D. Amino acid sequence of humanized variable part of light chain. Nucleotides or amino acids modified for humanization purposes are underlined.

FIG. 14: A: Binding of scFv16D3 and humanized scFv16D3 to PlGF; B: Inhibition of huPlGF-2 binding to its receptor huFlt-1 by scFv16D3 and humanized scFv16D3 (B).

FIG. 15: A: Amino acid sequence of scFv of murine antibody 16D3; B: Amino acid sequence of humanized scFv of antibody 16D3. Regions outside heavy and light chain variable regions are underlined.

FIG. 17: A: Binding of humanized Fab 16D3 to huPlGF with an ELISA test in accordance with an embodiment of the present invention; B: Inhibition of huPlGF-2 binding to its receptor huFlt-1 by humanized Fab16D3

DEFINITIONS

Figure 1:
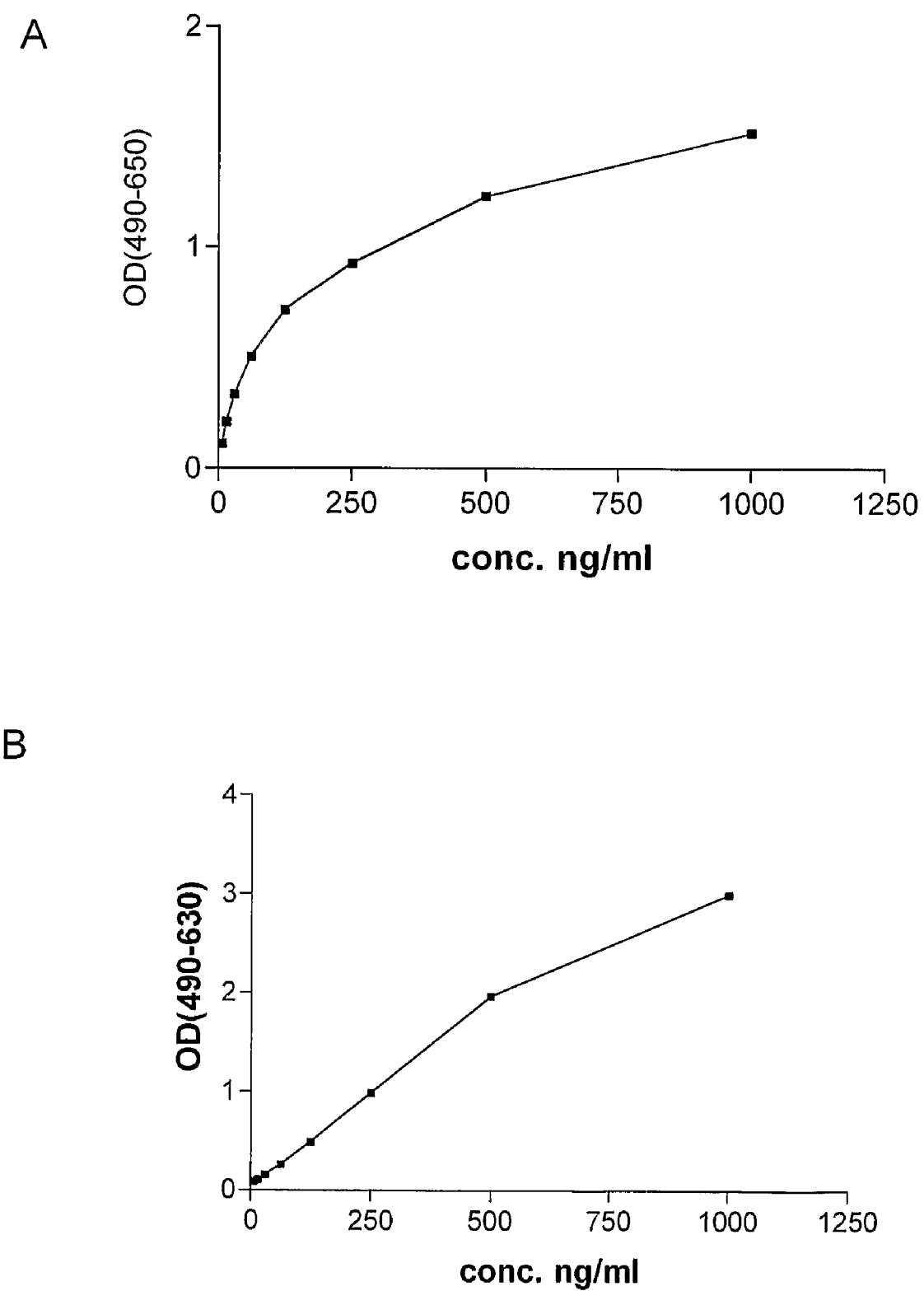
FIG. 1: Binding of antibody 16D3 (A) or humanized antibody 16D3 (hu16D3) (B) to human PlGF-2 (produced in Pichia) with an ELISA test in accordance with an embodiment of the present invention.

The term '16D3' as used herein refers to the monoclonal antibody against PlGF produced by the cell line deposited by Thromb-X under the terms of the Budapest Treaty with the Belgian Coordinated Collections of Microorganisms-BCCM™/LMBP Collection (Universiteit Gent, Technologiepark 927, B-9052 Gent-Zwijnaarde, Belgium) on Mar. 29, 2005 under accession number LMBP 6399CB.

The term "antibody fragment" refers to a sub-part of an antibody molecule which alone, or in combination with other fragments, is capable of binding to the antigen against which the corresponding antibody was raised. Typical antibody fragments are Fab, Fab', F(ab')$_2$, Fv or scFv, which often retain an affinity for the antigen which is comparable to the complete antibody. Smaller fragments include complementarity determining regions or CDRs such as CDR1, CDR2 and CDR3 of the heavy or light chain and/or combinations of two or more thereof.

The term "derivative" is used herein to refer to an antigen-binding molecule which corresponds to a modification of the original antibody (e.g. as produced by a hybridoma cell line) or fragment thereof, without significantly affecting the binding to the antigen. Typical modifications include modifications of the amino acid sequence of the original antibody or modifications of the functional groups present on the amino acid sequence, e.g. in the context of humanization, for the binding of the antibody or fragment thereof to other molecules such as labels or beads, or for the modification of glycosylation. Thus, derivatives include but are not limited to humanized antibodies, hybrid antibodies, antibodies or other antigen-binding molecules which have been obtained by grafting or introducing one or more of the variable regions and/or CDRs of the original antibody on the backbone of another antibody or fragment of the same or a different species. Derivatives of an antibody include alternative structures of one or more CDRs of the antibody resulting in an antigen-binding molecule such as a synthetic polypeptide.

A "humanized antibody or antibody fragment" as used herein, refers to an antibody molecule or fragment thereof in which, compared to the original antibody, amino acids have been replaced in order to more closely resemble a human antibody. The majority of these substitutions will be in the backbone of the antibody or antibody fragment, i.e. in non-antigen binding regions. However, it is envisaged that within the CDRs, amino acids which do not or hardly take part in the binding to the antigen can also be substituted.

A "Reshaped" antibody or antibody fragment or a "hybrid antibody" as used herein, refers to an antibody which comprises parts of at least two different antibodies, which can optionally be of the same or of a different species. Typically, a human hybrid antibody can be a human constant region of one antibody linked to a humanized variable region of another antibody (which is directed against the antigen of interest) or a human antibody backbone of one antibody in which amino acid sequences in the antigen binding regions have been replaced with sequences from another antibody e.g. a non-human antibody directed against a human antigen of interest. More particularly the antigen-binding regions of one (usually non-human) antibody having an affinity for an antigen of interest, such as one or more CDRs or variable regions or parts thereof, are introduced into the backbone of another (usually human) antibody (e.g. CDR-grafted antibodies).

The term "homology" or "homologous" as used herein with reference to two or more antigen-binding molecules of the present invention refers to the ability of the antigen-binding molecules to bind to the same antigen, more particularly to the same epitope. The ability of two antigen-binding molecules to bind to the same epitope can be assessed by determining whether the antigen-binding molecules can compete with each other for the binding to the same antigen, e.g. in a competitive binding assay. The binding to the antigen of homologous antigen-binding molecules should be of similar specificity.

The "sequence identity" of two sequences as used herein relates to the number of positions with identical nucleotides or amino acids divided by the number of nucleotides or amino acids in the shorter of the sequences, when the two sequences are aligned. Preferably said sequence identity is higher than 70%-80%, preferably 81-85%, more preferably 86-90%, especially preferably 91-95%, most preferably 96-100%, more specifically is 100%. In view of the generally limited contribution of the backbone of the variable regions to the binding with the antigen, sequence identity is most commonly specified herein with regard to the sequence within the complementarity determining regions or CDRs, i.e. with regard to the nucleotide sequences encoding and the amino acid sequences which constitute the CDRs. Thus, when a sequence is specified to have e.g. an 80% sequence identity over a specific sequence 'within the CDRs' it is intended to provide the sequence identity between the two sequences only with regard to the sequences making up the CDRs.

The term "PlGF" is used herein to refer to placental growth factor. PlGF has been found to occur mainly in two splice variants or isoforms, PlGF-1 of 149 amino acids and PlGF-2 of 170 amino acids, which comprises a 21 amino acid insertion in the carboxy-terminal region, but also other isoforms have been found.

The term 'inhibitory' when referring to an antibody to PlGF or fragment or derivative thereof is used to indicate that the antibody, fragment or derivative is capable of inhibiting the binding of PlGF to its receptor Flt-1.

DETAILED DESCRIPTION

The present invention will be described with reference to certain embodiments and to certain Figures but the present invention is not limited thereto but only by the claims.

The present invention relates to antigen-binding molecules, particularly monoclonal antibodies, fragments or derivatives thereof which bind to the same epitope of PlGF as the antibody referred to herein as antibody 16D3. "Antibody 16D3", produced by cell line LMBP 6399CB, was raised against PlGF of human origin, and binds human PlGF (both isoforms PlGF-1 and PlGF-2). Antibody 16D3 inhibits the binding of human PlGF to its receptor flt-1, inhibiting PlGF-activity. The 16D3 antibody itself and fragments or derivatives thereof, as well as nucleotide sequences encoding the antibody, fragments or derivatives, can thus be used for the inhibition of PlGF both in a therapeutic context and in an animal model for testing or screening purposes. Alternatively, the antibody can be used for detection and/or quantification of PlGF either in vivo, ex vivo, or in vitro. Thus, the present invention provides different applications of the antigen-binding molecules of the invention and the nucleotide sequences encoding them. The invention further relates to methods of producing the antigen-binding molecules of the invention, and to cell lines capable of producing these antigen-binding molecules.

A first aspect of the present invention relates to cell lines producing the antigen-binding molecules of the invention, more particularly cell lines producing monoclonal antibodies capable of binding to the same antigen as 16D3 or fragments or derivatives thereof. A particular embodiment of this aspect of the invention is the hybridoma cell line also referred to as 'cell line 16D3' which produces the monoclonal antibody 16D3 and which was deposited with the BCCM/LMBP (Belgian Co-ordinated Collections of Microorganisms/Plasmid Collection Laboratorium voor Moleculaire Biologie, University of Ghent K. L. Ledeganckstraat 35, B-9000 Ghent, BE by Thromb-X on Mar. 29, 2005 as deposit number LMBP 6399CB. The present invention further provides cell lines producing monoclonal antibodies derived from monoclonal antibody 16D3. Such cell lines can be obtained by modifying the coding sequence for monoclonal antibody 16D3, most particularly the coding sequence encoding the non-antigen binding regions of 16D3. Methods of determining the nature of the modifications to be made, and examples of suitable modifications are described herein.

A second aspect of the invention relates to antigen-binding molecules capable of binding to the same antigen as antibody 16D3. More particularly, the invention relates to the antibody named 16D3 produced by the cell line 16D3 described above and homologues, fragments and derivatives thereof capable of binding PlGF and inhibiting PlGF activity.

Thus a particular embodiment of the present invention provides the anti-human PlGF antibody monoclonal antibody 16D3 as produced by cell line LMBP 6399CB, and fragments of this antibody. Monoclonal antibody 16D3 is characterized by the amino acid sequence of the variable regions of its heavy and light chains as disclosed in SEQ ID NO: 2 and SEQ ID NO: 4, respectively.

According to a specific embodiment, the present invention relates to fragments, more particularly antigen-binding fragments of antibody 16D3. Such fragments include, but are not limited to Fab, Fab', F(ab')$_2$, CDR's, peptides with a sequence of a part of the antibody or its CDRs, single variable domains and combinations of these. Fab, Fab' and F(ab')$_2$ fragments can be generated by proteolytic digestion of monoclonal antibodies using methods well known in the art, such as described by Stanworth et al., *Handbook of Experimental Immunology*, (1978), vol. 1 chapter 8 (Blackwell Scientific Publications). Such fragments, which retain the ability to bind the antigen, have lost a number of properties of the parent antibody, such as complement activation or capacity to bind to Fc gamma receptors. More specifically the present invention provides fragments comprising the variable regions of the heavy and light chains of 16D3 corresponding to SEQ ID NO: 2 and SEQ ID NO: 4 respectively. A further particular embodiment of the invention relates to fragments comprising the complementarity determining regions (CDRs) of 16D3 and derivatives thereof. The two most commonly followed methods for identifying CDRs are IMGT and KABAT, and fragments comprising more than one of either type of CDR of 16D3 are envisaged within the context of the invention, as well as derivatives of 16D3 comprising these fragments or CDRs. According to the IMGT identification of CDRs, the CDR regions within the variable regions of 16D3 correspond to SEQ ID NO: 17 (GYTFTDYY), SEQ ID NO: 18 (IYPGS-GNT); SEQ ID NO:19 (VRDSPFFDY), SEQ ID NO: 20 (QSLLNSGMRKSF), SEQ ID NO: 21 (WAS) and SEQ ID NO: 22 (KQSYHLFT). Thus, the present invention provides for fragments of antibody 16D3 comprising one or more of the CDRs of 16D3 as provided in SEQ ID NO: 17 to SEQ ID NO: 22.

A further specific embodiment of the invention provides fragments of 16D3 which are soluble or membrane anchored single-chain variable parts of 16D3. A single-chain variable fragment (scFv) is a genetically engineered antibody fragment that usually consists of the variable heavy chain (VH) and light chain (VL) of an immunoglobulin, or parts thereof, joined together by a flexible peptide linker. Optionally, scFvs comprise the CDR regions of the antibody of interest and framework regions of another antibody. The amino acid sequence of the scFv framework and/or CDR regions is optionally humanized to reduce antigenicity for use as a pharmaceutical in humans. The invention provides a scFv of 16D3 and a humanized version thereof comprising SEQ ID NO: 24 and SEQ ID NO: 26, respectively. Methods for obtaining single-chain variable parts of antibodies are known to the skilled person and are described in example 6 herein. For instance the method can include amplification of the DNA sequences of the variable parts of human heavy and light chains in separated reactions and cloning, followed by insertion of a fifteen amino-acid linker sequence, for instance (Gly4 Ser)3 between VH and VL by a two-steps polymerase chain reaction (PCR) (see for instance Dieffenbach and Dveksler, "PCR Primer, a laboratory manual" (1995), Cold Spring Harbour Press, Plainview, N.Y., USA). The resulting fragment can then be inserted into a suitable vector for expression of single-chain variable fragment as soluble or phage-displayed polypeptide. This can be achieved by methods well known to those skilled in the air, such as described by Gilliland et al., *Tissue Antigens* (1996) 47:1-20.

The present invention also provides fragments of 16D3 which are antigen-binding peptides representative of the hypervariable regions of antibody 16D3 or combinations thereof. Such peptides can be obtained by synthesis using an applied biosystem synthesizer, for instance a polypeptide synthesizer such as model 9050 available from Milligen (USA) or a model from a related technology.

A further embodiment of the invention relates to derivatives of antibody 16D3 or fragments thereof. More particularly, the invention relates to antibodies comprising a variable heavy chain region and or a variable light chain region as disclosed in SEQ ID NO: 2 and SEQ ID NO: 4, respectively, but of which the constant regions are different from those in 16D3. Additionally or alternatively, the derivatives of antibody 16D3 of the present invention comprise at least two of the CDRs of 16D3 as provided in SEQ ID NO: 17 (GYTFTDYY), SEQ ID NO: 18 (IYPGSGNT); SEQ ID NO: 19 (VRDSPFFDY), SEQ ID NO: 20 (QSLLNSGMRKSF), SEQ ID NO: 21 (WAS) and SEQ ID NO: 22 (KQSYHLFT), while the framework regions between the CDRs and/or the constant regions are different.

According to one embodiment of the invention, derivatives of antibody 16D3 or fragments thereof are provided having at least 80%, particularly at least 85%, more particularly at least 90%, most particularly at least 95% sequence identity with the heavy and light chain variable region of 16D3 provided in SEQ ID NO:2 and SEQ ID NO:4 respectively. Most particularly the present invention provides derivatives of antibody 16D3 or fragments thereof comprising a heavy chain variable region and/or a light chain region having at least 80%, particularly at least 85%, more particularly at least 90%, most particularly at least 95% sequence identity with SEQ ID NO: 2 and SEQ ID NO: 4, respectively within the CDR regions. Sequence identity within the framework regions can be, but is not limited to, less than 80%. Also envisaged are derivatives comprising at least two CDRs which have at least 80%, particularly at least 85%, more particularly at least 90%, most particularly at least 95% sequence identity with the sequences of SEQ ID NO: 17 to 22, respectively.

According to a further embodiment, the invention provides derivative of a scFv of 16D3 comprising a sequence having at least 80%, particularly at least 85%, more particularly at least 90%, most particularly at least 95% sequence identity with SEQ ID NO: 24 and a sequence having at least 80%, particularly at least 85%, more particularly at least 90%, most particularly at least 95% sequence identity with SEQ ID NO: 26, most particularly within the CDR regions.

According to another embodiment, the invention provides derivatives of 16D3 or fragments thereof which are humanized. Such humanized derivatives of 16D3 are homologues in that they retain their binding affinity for PlGF. According to a particular embodiment, the humanized derivatives of 16D3 also retain the ability to inhibit PlGF activity. Humanization of non-human antibodies is a achieved by a replacement of one or more amino acids in the backbone of the antibody, i.e. those amino acids not involved in the binding of the antibody to the antigen, so as to resemble more closely the backbone of a human antibody. Different types or levels of humanization are envisaged. Particular embodiments of the invention relate to antibodies or fragments in which entire regions, more particularly the constant region(s) of the non-human antibody or fragment is(are) replaced by the constant region(s) of a human antibody, so as to result in chimeric (e.g. human/murine) antibodies or fragments. Further particular embodiments are antibodies where the antigen-binding amino acids (e.g. two or more CDRs) of the non-human antibody against PlGF is introduced into the backbone of a human antibody (e.g. CDR-grafted antibodies). Methods for associating the binding complementarity determining region ("CDR") from the non-human monoclonal antibody with human framework regions—in particular the constant C region of human gene—are known to the skilled person, such as disclosed by Jones et al. in *Nature* (1986) 321:522 or Riechmann in *Nature* (1988) 332:323. Alternatively replacement of a more limited number of amino acids of the non-human anti-PlGF antibodies of the invention is also envisaged. Particular embodiments of the invention relate to antibodies comprising humanized variable heavy and/or light chain regions of FIG. 9 or parts thereof and antibodies comprising at least two, more particularly three to five, most particularly all six CDRs of SEQ ID NO. 17 to SEQ ID NO. 22. Further embodiments of the invention relate to humanized antibodies comprising variable heavy and/or light chain regions having at least 80%, particularly at least 85%, more particularly at least 90%, most particularly at least 95% sequence identity with SEQ ID NO: 6 and SEQ ID NO: 8, respectively. Alternatively, the present invention provides humanized antibodies comprising at least two, more particularly three to five, most particularly six CDRs having at least 80%, particularly at least 85%, more particularly at least 90%, most particularly at least 95% sequence identity with SEQ ID NO: 17 to 22, respectively.

The present invention thus relates to humanized and/or chimeric or hybrid antibodies derived from the murine antibody 16D3. In a particular embodiment, specific amino acids of the murine antibody 16D3 are mutated in order to eliminate immunogenic amino acids. Therefore, in a particular embodiment, the present invention relates to antigen-binding molecules comprising a heavy chain variable part amino acid sequence according to SEQ ID NO: 2 wherein one or more of the following amino acids has been changed: 12V, P9A, K40A and/or T111L. Additionally or alternatively, the humanized antibodies derived from antibody 16D3 are antigen-binding molecules comprising a light chain variable part amino acid sequence according to SEQ ID NO: 4, wherein one or more of the following amino acids has been changed: S5T, S9D, A15L, K18R, R22N and/or L89V. Thus according to a particular embodiment, the invention provides antigen-binding molecules comprising both a heavy chain variable part amino acid sequence according to SEQ ID NO: 2, wherein one or more of the following amino acids has been changed: 12V, P9A, K40A and/or T111L and a light chain variable part amino acid sequence of SEQ ID NO: 4 wherein one or more of the following amino acids has been changed: S5T, S9D, A15L, K18R, R22N and/or L89V.

In another embodiment, the antibody is further humanized in that the (humanized) variable light and/or heavy chains of the murine antibody 16D3 are grafted in a human immunoglobulin frame or are coupled to the constant region of a human antibody, more in particular to a human IgG constant region. Particularly suited in this respect are IgG1κ (IgG1-kappa), which are capable of activating Natural killer cells in the body. In a particular embodiment, the present invention thus relates to a hybrid Hu16D3—IgG1κ. An alternative embodiment of the present invention is a hybrid Hu16D3—IgG4κ hybrid. Human IgG antibodies (and thus also hybrid antibodies obtained using human IgG backbone and/or constant regions) exhibit a prolonged half-life time, thus providing very stable plasma levels and allowing for a drastic reduction in the frequency of administration. Further, the use of humanized antibodies or derivatives carries a minimal risk of inducing immune responses.

Further embodiments of the present invention relate to antigen-binding molecules which are homologous to antibody 16D3 or fragments thereof, i.e. antigen-binding molecules that bind to the same epitope as antibody 16D3. In one embodiment the homologous antigen-binding molecules are produced by on purpose immunization in animals, more particularly in mouse, for instance by injecting PlGF in mice and then fusing the spleen lymphocytes with a mouse myeloma cell line, followed by identifying the cell cultures producing anti-PlGF antibodies (e.g. by screening on binding to PlGF) and cloning them. Optionally further selection of the antibodies is performed based on reactivity with the 16D3 epitope, or competition with antibody 16D3 or a fragment thereof.

Yet another aspect of the invention thus relates to methods for producing the antigen-binding molecules of the present invention. These methods include, but are not limited to, the methods of humanization to antibody 16D3 as provided in the Examples section herein.

Yet another aspect of the present invention relates to the provision of nucleotide sequences encoding the antigen-binding molecules of the present invention, most particularly the antigen-binding regions thereof. Particular embodiments of the invention relate to the nucleotide sequences encoding the variable heavy chain region and the light chain variable region defined by SEQ ID NO: 2 and SEQ ID NO: 4, respectively, such as, but not limited to the nucleotide sequences of SEQ ID NO: 1 and SEQ ID NO: 3, corresponding to the sequences of cell line 16D3 encoding the heavy and light chain region of antibody 16D3. Also within the context of the present invention nucleotide sequences are provided which encode one or more of the CDR regions of monoclonal antibody 16D3 as identified in SEQ ID NOs. 17 to 22. Particular embodiments of the invention include the sequence encoding scFvs and humanized scFvs of 16D3 such as but not limited to SEQ ID NO: 23 and SEQ ID NO: 25, respectively. The invention also provides nucleotide sequences encoding the derivatives of 16D3 and fragments thereof, described herein. The present invention also provides probes and primers capable of specifically hybridizing to the nucleotide sequences referred to above, such as, but not limited to the primers described in the Examples section.

The present invention also includes nucleotide sequences which are complementary to the sequences encoding the monoclonal antibodies, fragments or derivatives thereof, described herein.

Yet another aspect of the present invention, relates to the therapeutic application of the antigen-binding molecules of the present invention. The present invention thus provides the use of the antigen-binding molecules of the present invention as a medicament. In this regard, the invention provides pharmaceutical compositions, comprising one or more of the antigen-binding molecules of the invention, for the prevention or treatment of diseases or disorders in which angiogenesis contributes to the pathology of the disease or disorder. Accordingly methods of treatment and/or prevention of diseases in which angiogenesis contributes to the pathology of the disease or disorder comprising administering to a mammal in need of such treatment or prevention, a therapeutically effective amount of a composition comprising one or more of the antigen-binding molecules described herein.

In such diseases, the angiogenesis is also referred to as 'pathological angiogenesis'. Examples of such pathological angiogenesis include the angiogenesis observed in pathology of blood vessels (atherosclerosis, hemangioma, hemangioendothelioma), of bone and joints (rheumatoid arthritis, synovitis, bone and cartilage destruction, osteomyelitis, pannus growth, osteophyte formation, neoplasms and metastasis), of skin (warts, pyogenic granulomas, hair growth, Kaposi's sarcoma, scar keloids, allergic oedema, neoplasms), of liver, kidney, lung, ear and other epithelia (inflammatory and infectious processes including hepatitis, glomerulonephritis, pneumonia, asthma, nasal polyps, otitis, and transplantation, regeneration, neoplasms and metastasis in these organs), in certain pathologies of the uterus, ovary and placenta (dysfunctional uterine bleeding e.g. due to intra-uterine contraceptive devices, follicular cyst formation, ovarian hyperstimulation syndrome, endometriosis, neoplasms), pathologies in the brain or nerves (neoplasms and metastasis), certain heart and skeletal muscle afflictions (e.g. due to work overload), pathological conditions of adipose tissue (obesity) and endocrine organs (thyroiditis, thyroid enlargement, pancreas transplantation). Pathological angiogenesis can also contribute to diseases of hematopoiesis (AIDS, Kaposi), hematologic malignancies (leukemias, etc.).

In a number of diseases of the eye pathological angiogenesis is believed to be an important factor, and thus treatment with the antigen-binding molecules of the present invention is envisaged. In the 'retinal ischemic diseases' the retina's supply of blood and oxygen is decreased, the peripheral portions of the retina lose their source of nutrition and stop functioning properly. Common causes of retinopathy are central retinal vein occlusion, stenosis of the carotid artery, diabetes (diabetic retinopathy) and anemia (sickle cell retinopathy). Retinopathy is also observed in premature infants (retinopathy of prematurity). Diabetic retinopathy is a major cause of visual loss in diabetic patients. In the ischemic retina the growth of new blood vessels occurs (neovascularisation). These vessels often grow on the surface of the retina, at the optic nerve, or in the front of the eye on the iris. The new vessels cannot replace the flow of necessary nutrients and, instead, can cause many problems such as vitreous hemorrhage, retinal detachment, and uncontrolled glaucoma. These problems occur because new vessels are fragile and are prone to bleed. If caught in its early stages, proliferative diabetic retinopathy can sometimes be arrested with panretinal photocoagulation. However, in some cases, vitrectomy surgery is the only option. Other diseases of the eye in which angiogenesis is believed to play a critical role is are choroidal and other intraocular disorders, leukomalacia, and neoplasms and metastasis. Choroideal neovascularization is the growth of new blood vessels that originate from the choroid through a break in the Bruch membrane into the sub-retinal pigment epithelium (sub-RPE) or subretinal space. The location, growth pattern, and type (1 or 2) of CNV depend on the patient's age and the underlying disease. Bleeding and exudation occur with further growth, accounting for the visual symptoms. Choroidal neovascularization (CNV) is a major cause of visual loss. CNV is estimated to occur in 5-10% of myopes and occurs in virtually all choroidal ruptures during the healing phase; most involute spontaneously but in 15-30% of patients, CNV may recur and lead to a hemorrhagic or serous macular detachment with concomitant visual loss.

The term 'pulmonary hypertension' refers to a disorder in which the blood pressure in the pulmonary arteries is abnormally high. In the absence of other diseases of the heart or lungs it is called primary pulmonary hypertension. Diffuse narrowing of the pulmonary arterioles occurs as a result of pathological arteriogenesis followed by pulmonary hypertension as a response to the increased resistance to blood flow. The incidence is 8 out of 100,000 people. However, pulmonary hypertension can also occur as a complication of Chronic Obstructive Pulmonary Diseases (COPD) such as emphysema, chronic bronchitis or diffuse interstitial fibrosis and in patients with asthmatiform COPD. The incidence of COPD is approximately 5 out of 10,000 people.

Yet a further example of a disease in which angiogenesis contributes to the pathology of the disease, and which is envisaged for treatment with the antigen-binding molecules of the present invention is the group of inflammatory disorders. 'Inflammation' as used herein means the local uncontrolled reaction to injury (i.e. physical, chemical or as a result of infection) of living tissues, especially the local reaction of the small blood vessels, their contents, and their associated structures. The passage of blood constituents through the vessel walls into the tissues is the hallmark of inflammation, and the tissue collection so formed is termed the exudate or oedema. Any noxious process that damages living tissue such as but not limited to infection with bacteria, excessive heat, cold, mechanical injury such as crushing, acids, alkalis, irradiation, or infection with viruses can cause inflammation irrespective of the organ or tissue involved. Such 'inflammatory diseases' include reactions ranging from burns to pneumonia, leprosy, tuberculosis, and rheumatoid arthritis.

Post-operative adhesion formation (POA) is a frequent surgical complication in gynecological, pelvic, and cardiological surgeries. Surgical trauma to the tissues often causes permanent scar formation which connects the traumatized tissue to another organ. Thus at the site of such damage, internal tissues that normally remain separate. often become joined together. Complications arising form adhesion formation are intestinal obstructions, small bowel obstructions, chronic pelvic pain, and infertility in women. The term "adhesion formation" in its medical sense refers to conglutination, the process of adhering or uniting of two surfaces or parts. For example, the union of the opposing surfaces of a wound, or opposing surfaces of peritoneum. Also, adhesions, in the plural, can refer to inflammatory bands that connect opposing serous surfaces. The term adhesion, as used herein, also includes fibrinous adhesions, which are adhesions that consist of fine threads of fibrin resulting from an exudate of plasma or lymph, or an extravasation of blood. Keloid, a smooth overgrowth of fibroblastic tissue that arises in an area of injury or, occasionally, spontaneously is also a form of adhesion. It has been shown that the inhibition of placenta growth factor (PlGF) leads to a remarkable suppression of postoperative adhesion formation (WO03063904).

It has moreover been demonstrated that diseases characterized by bone resorption, such as, but not limited to osteoporosis, can benefit from inhibition of PlGF (WO2004002524).

Thus, according to a specific embodiment the antigen-binding molecules of the present invention are particularly suited for the treatment and/or prevention of tumor growth and metastasis, diseases of the eye, inflammation, adhesion formation, and pulmonary hypertension.

A further particular embodiment of the invention relates to the use of the antigen-binding molecules of the present invention for the prevention and/or treatment of cancer, such as but not limited to cancer of the breast, lung, prostate, brain, liver, pancreas, colon, kidney, uterus or bone marrow. More particularly, the invention relates to the use of the antigen-binding molecules of the present invention for the prevention and/or treatment of solid tumors such as but not limited to colon cancer, breast cancer, pancreatic cancer, and melanomas. More particularly data are provided herein demonstrating that the antibodies of the present invention are particularly suited for obtaining regression of human pancreatic tumors. The antibodies of the present invention are demonstrated to significantly reduce tumor size in vivo, whereby reductions in size of up to about 50% are demonstrated. Thus, the present invention provides methods and pharmaceutical compositions for reducing tumor size at least 20%, more particularly at least 30%, most particularly at least 50%.

A further particular embodiment of the invention relates to the use of the antigen-binding molecules of the present invention in the treatment or prevention of bone disorders and more specifically for the treatment of conditions where there is an enhanced bone resorption such as for example osteoporosis or osteomalacia.

Accordingly, the present invention relates to the use of the antigen-binding molecules of the present invention for the manufacture of a medicament for the treatment of the above-mentioned diseases.

In important aspect of the present invention is that the antibodies, fragments and derivatives thereof allow the treatment and/or prevention of the above-mentioned diseases without the side-effects attributed to or expected with other anti-angiogenic treatments, more particularly alternative treatments targeting angiogenic factors, such as VEGF. Preclinical safety trials with recombinant human anti-VEGF antibodies demonstrated as early as 1999 that inhibition of VEGF results in inhibition of physiological angiogenesis, more particularly neovascularization in longitudinal bone growth and corpora lutea formation (Ryan et al., 1999) Toxicologic pathology 27(1):78-86). Recent studies describe that VEGF inhibitors cause regression of vessels in healthy trachea and thyroid glands, which may lead to organ dysfunction (Baffert et al, 2004, Circ Res 94:984-992; Inai et al., 2004 Am J Pathol 165:35-52). Nevertheless bevacizumab, an anti-human VEGF antibody is currently on the market as suppressor of angiogenesis, despite its observed effects on wound-healing, blood-pressure and risk of thrombosis, because of the overall efficacy of this anti-angiogenic approach on tumor regression. The anti-PlGF antibodies and derivatives of the present invention allow the inhibition of undesired angiogenesis without these observed side-effects on blood pressure, wound healing, risk of thrombosis, and vessel regression in healthy organs.

A particular embodiment of the present invention relates to pharmaceutical compositions, comprising, as an active ingredient, the monoclonal antibody 16D3 or a fragment or derivative thereof, in admixture with a pharmaceutically acceptable carrier. The pharmaceutical composition of the present invention comprises a therapeutically effective amount of one or more of the antigen-binding molecule. Similarly, the present invention provides for methods of treatment and/or prevention which comprise the administration of a therapeutically effective amount one or more of the antigen-binding molecule of the present invention.

A therapeutically effective amount as used herein means an amount within the range from about 0.5 mg per kilogram of body weight (mg/kg) to about 50 mg/kg, more preferably from about 1 mg/kg to about 10 mg/kg of the mammal to be treated. It will be appreciated that, in view of the long half-life time of most IgG human antibodies, the antigen-binding molecules of the present invention which are monoclonal antibodies of this class will enjoy a periodicity of treatment which participates in the comfort of the patient.

According to yet another aspect of the invention, pharmaceutical compositions are provided which comprise the antigen-binding molecules of the present invention and another anti-angiogenic agent, as well as methods of treatment providing for a simultaneous or sequential administration of the antigen-binding molecules of the present invention and another anti-angiogenic agent. Indeed, the present invention demonstrates an additive effect of the antigen-binding molecules of the present invention and other anti-angiogenic agents, such as anti-VEGF antibodies on the inhibition of tumor growth. More particularly it is demonstrated that the combined use of the 16D3 antibody of the present invention and Avastin® is capable of reducing the tumor size of up to about 70%, while increased dosages of either Avastin® alone or the anti-PlGF antibody do not reach a reduction of tumor size of more than 55% in the same conditions. Suitable other anti-angiogenic products, as well as their usual dosage depending on the class to which they belong, are well known to those skilled in the art. Examples of anti-angiogenic agents include inhibitors of VEGF acting directly on VEGF, such as the antibody directed against VEGF commercialized under the name Avastin™ or acting on the VEGF receptors. The antibodies of the present invention make it possible to decrease the dosage of e.g. VEGF inhibiting anti-angiogenic agents, known to induce a number of side effects as described above.

The pharmaceutical compositions of the present invention may further comprise, a therapeutically effective amount of other compounds/drugs active against the disease to be treated, more particularly other compounds/drugs useful in the treatment of tumour growth, inflammation, diseases of the eye and pulmonary hypertension.

Suitable pharmaceutical carriers for use in the pharmaceutical compositions of the invention are described for instance in Remington's Pharmaceutical Sciences 16$^{th}$ ed. (1980) and their formulation is well known to those skilled in the art. They include any and all solvents, dispersion media, coatings, antibacterial and antifungal agents (for example phenol, sorbic acid, chlorobutanol), isotonic agents (such as sugars or sodium chloride) and the like. Additional ingredients may be included in order to control the duration of action of the monoclonal antibody active ingredient in the composition. Control release compositions may thus be achieved by selecting appropriate polymer carriers such as for example polyesters, polyamino acids, polyvinyl pyrrolidone, ethylene-vinyl acetate copolymers, methylcellulose, carboxymethylcellulose, protamine sulfate and the like. The rate of drug release and duration of action may also be controlled by incorporating the monoclonal antibody active ingredient into particles, e.g. microcapsules, of a polymeric substance such as hydrogels, polylactic acid, hydroxymethylcellulose, polymethyl methacrylate and the other above-described polymers. Such methods include colloid drug delivery systems like liposomes, microspheres, microemulsions, nanoparticles, nanocapsules and so on. Depending on the route of administration, the pharmaceutical composition comprising the active ingredient may require protective coatings. The pharmaceutical form suitable for injectionable use include sterile aqueous solutions or dispersions and sterile powders for the extemporaneous preparation thereof. Typical carriers therefore include biocompatible aqueous buffers, ethanol, glycerol, propylene glycol, polyethylene glycol and mixtures thereof.

The antigen-binding molecules of the present invention may be provided to a patient by any means well known in the art, i.e. orally, intranasally, subcutaneously, intramuscularly, intradermally, intravenously, intraarterially, parenterally or by catheterization.

According to a particular aspect of the present invention, the antigen-binding molecules of the present invention are administered by gene-therapy. Antibody-based gene therapy makes it possible to overcome a number of potential limitations associated with the administration of antibodies such as large-scale production, biodistribution, rapid blood clearance and poor retention of monovalent antibodies. In vivo production makes the antibodies less immunogenic and better tolerated and results in effective and persistant levels of Antigen-binding molecules or fragments thereof. Moreover, genetic approaches make it possible to provide the antigen-binding molecules with new functions. The feasibility of in vivo production and systemic delivery of monoclonal antibodies by different cells/tissues has been demonstrated using in vivo gene transfer by viral vectors (Pelegrin et al., 2004, Gene Ther 4: 347-356). The reduction of tumor growth in vitro and in vivo by gene-modification of fibrosarcoma cells with an anti-laminin antibody with antiangiogenic activity has also been demonstrated (Sanz et al. 2001, Cancer Immunol Immunother 50:557-565).

Thus, according to this embodiment, the present invention provides nucleotides encoding the antigen-binding molecules of the present invention for use in gene therapy in the treatment of the diseases characterized by pathological angiogenesis described herein. Particularly, the present invention provides for compositions comprising nucleotide sequences encoding the variable heavy chain region defined by SEQ ID NO: 2 and/or nucleotide sequences encoding the light chain variable region defined by SEQ ID NO: 4, for use in gene therapy. More particularly, the present invention provides compositions comprising the nucleotide sequence of SEQ ID NO: 1 and/or SEQ ID NO: 3, corresponding to the sequences of cell line 16D3 encoding the heavy and light chain region of antibody 16D3. Also within the context of the present invention compositions comprising nucleotide sequences are provided which encode one or more of the CDR regions of monoclonal antibody 16D3 as identified in SEQ ID NOs. 17 to 22. Particular embodiments of the invention include the sequence encoding scFvs and humanized scFvs of 16D3 such as but not limited to SEQ ID NO: 23 and SEQ ID NO: 25, respectively.

The method of treatment and/or prevention according to the invention may include further treatment or prevention of the same pathological angiogenesis condition by administrating, preferably by sequentially administrating, to the patient a therapeutically effective amount of a anti-angiogenic or anti-tumour agent such as disclosed hereinabove under the heading of pharmaceutical compositions. Sequentially, as used herein, means that the ligand of the present invention and the known anti-angiogenesis agent are administered to the patient sequentially but not simultaneously.

Yet another aspect of the present invention relates to the use of the antigen-binding molecules of the invention for the immunological detection of PlGF in human samples and as components of kits suitable for such detection. Methods of immunological detection of an antigen are known in the art and include, but are not limited to, EIA, ELISA and RIA and immunohistochemical methods. The binding of the murine antibodies of the present invention to the PlGF antigen can be detected indirectly e.g. by way of a labeled anti-mouse antibody. Alternatively the antibodies or fragments thereof can be labeled directly. A specific embodiment of this aspect of the invention relates to the use of the antibodies against PlGF and antigen-binding fragments thereof in the identification of patients susceptible to a treatment with anti-PlGF. This is of particular interest in the treatment of cancer.

Yet another aspect of the present invention relates to the use of the antigen-binding molecules of the present invention as a diagnostic tool. It has been demonstrated in the art that in a number of pathological conditions PlGF expression is upregulated. More particularly, a number of tumors have been demonstrated to over-express PlGF. The humanized antibodies or antibody fragments of the present invention can be used in the diagnosis of these pathological conditions e.g. by imaging techniques in which the antibodies or antigen-binding fragments of the invention are labeled and visualized in vivo. A variety of labels for imaging the binding of the antigen-binding molecules of the present invention in vivo are known in the art and include, but are not limited to optical (e.g. fluorescent), metal, and magnetic labels, each requiring specific (radiation and) detection devices. A particular embodiment of this aspect of the invention relates to the use of the antibodies of the invention in predicting prognosis of the disease and deciding treatment regimen.

Yet another aspect of the present invention relates to the use of the antigen-binding molecules of the present invention in animal models in the screening of compounds for use in combination with anti-PlGF therapy. Such models include but are not limited to tumor models whereby growth and development of human tumor cells in nu/nu mice is investigated. Combined administration of the compound to be tested and the antibody or fragment of the present invention make it possible to identify whether the compound has an additive effect to the effect observed upon administration of the antibodies or fragments of the invention alone. Other aspects such as counter-effectiveness or toxicity of a compound in combination with an anti-PlGF antibody can also be determined in this way.

Besides the therapeutic application described above, the nucleotide sequences of the present invention described above are useful in the production of antibodies and other antigen-binding fragments, e.g. by recombinant methods. Thus, the present invention further provides methods for producing recombinant antibodies and antibody fragments, including cloning and manipulation of antibody genes, production of scFv and other antigen-binding fragments using the nucleotide sequences described herein. The protocol of these methods is available in the alt. Additionally, the probes specifically hybridizing to the nucleotide sequences of the present invention can be used to screen for expression of the antibodies and antibody fragments of the present invention.

The present invention is further described by the following examples which are provided for illustrative purposes only.

EXAMPLES

Example 1

Production and Characterization of Murine Anti-Human PlGF Antibodies (16D3)

1. Immunization of Mice and Fusion

Monoclonal antibodies against human PlGF were produced essentially as described by Galfré and Milstein (Galfré F, Milstein C. Preparation of monoclonal antibodies: strategies and procedures. Method Enzymol 1981; 73: 3-46). Briefly, PlGF knock-out mice (Luttun et al., 2002, Biochem Biophys Res Comm 295(2):428-34, Carmeliet et al. (2001), Nat Med 7:575-593 or WO01/85796) were immunized by subcutaneous injection of 50 µg recombinant human PlGF-2 (produced in Pichia) in Complete Freund's adjuvant, followed two weeks later by subcutaneous injection with 50 µg recombinant human PlGF in incomplete Freund's adjuvant. Blood samples (about 100 µl) were collected from the tails of the mice after 10 days. The sera were tested for anti-huPlGF antibodies by ELISA using microtiter plates coated with human PlGF as capture, application of diluted sera (from 1/500 to 1/8000), and horseradish peroxidase (HRP)-conjugated goat-anti-mouse IgG for tagging.

After an interval of at least 6 weeks, the mice (with high positive responses) were boosted intraperitoneally with 50 µg recombinant human PlGF in saline on days 4 and 2 before the cell fusion.

Spleen cells were isolated and fused with Sp2/0-Ag14 myeloma cells. After selection in hypoxanthine, aminopterine, thymidine medium, positive clones were selected by application of culture supernatants into the ELISA as described above.

2. Purification of Antibodies on ProSep vA Ultra

Antibodies were purified from cell culture supernatant by affinity chromatography on ProSep vA Ultra (Millipore) according to the manufacturers protocol. Briefly, 150 mM NaCl was added to the supernatant and supernatant was loaded onto a ProSep vA Ultra column that was pre-equilibrated with PBS. The column was washed with PBS and bound protein eluted with 0.1 M glycine pH 2.8. Eluted protein was dialyzed ON to PBS. Purity of the eluted protein was checked under reducing and non-reducing conditions by SDS-PAGE.

3. Binding of 16D3/hu16D3 (Obtained as Described in Example 2) to PlGF (See FIG. 1)

ELISA plates were coated ON with 1 µg/ml huPlGF-2 (Pichia) in PBS, 100 µL/Well, 4° C. After blocking with 1% BSA, 1 hr, RT, a dilution series of 16D3/hu16D3 was added, 100 µL/well, the antibody was allowed to bind for 1 hr, RT. Bound 16D3 was detected with Goat-anti-human or goat-anti-murine IgG-HRP (Sigma), 100 µL/well, 1 hr, RT. The assay was developed with OPD.

Figure 2:
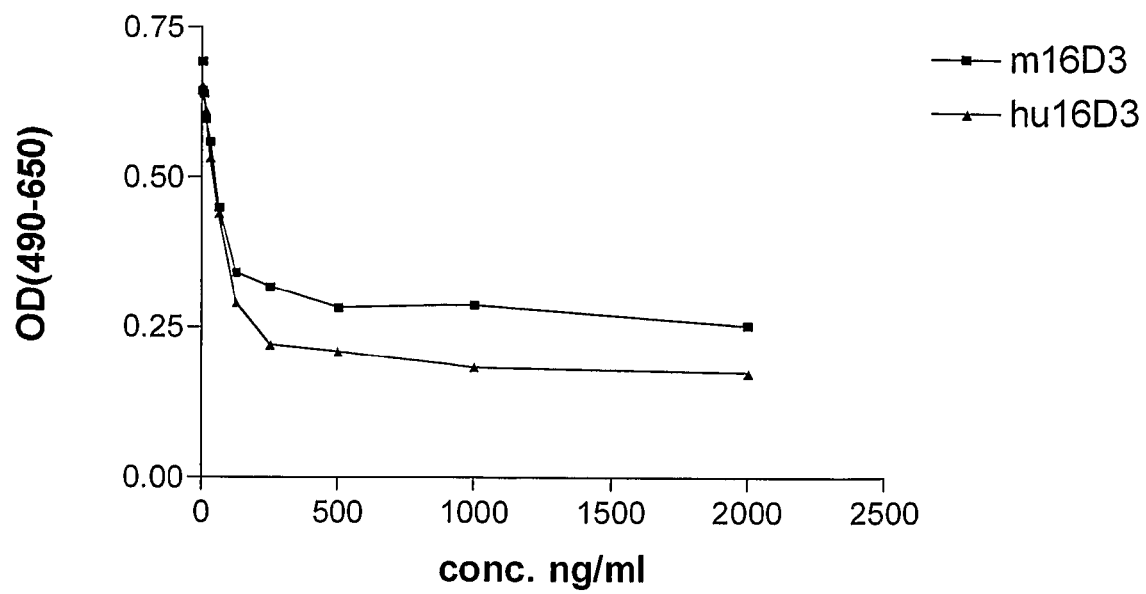
FIG. 2: Inhibition of PlGF-2 binding to human Flt-1 receptor by the antibody 16D3 (squares) or the humanized antibody 16D3 (triangles) with an ELISA test in accordance with an embodiment of the present invention.

4. Inhibition of PlGF Binding to huFlt-1 Receptor (See FIG. 2)

ELISA plates were coated ON with 1 µg/ml huFlt-1 (R&D Systems), 200 µL/well, ON, 4° C. After blocking with 1% BSA, 1 hr, RT, a dilution series of 16D3/hu16D3 was added, 100 µL/well, and an additional 100 µL/well of huPlGF-2 was added. After a 2 hour incubation at RT, bound PlGF was detected with Goat-anti-huPlGF (R&D Systems), 180 µL/well, 1 hr, RT, followed by an incubation with RAG-HRP (DAKO), 1 hr, RT. The assay was developed with OPD.

5. Further Characterization of 16D3 and Fab 16D3 with Biacore Experiments

Inhibition: rhuPlGF-2 (Pichia, Tex.) was immobilized on a CM5 chip using a EDC/NHS chemistry (amine coupling kit, Biacore), giving 412 RU. The 16D3 was injected followed by rhuFlt-1/Fc Chimera (R&D Systems). This was also performed with buffer instead of the mouse antibody. These were also injected over a negative control Flow channel and these values are already subtracted. This assay was performed in a phosphate buffer at pH 9.6.

Figure 3:
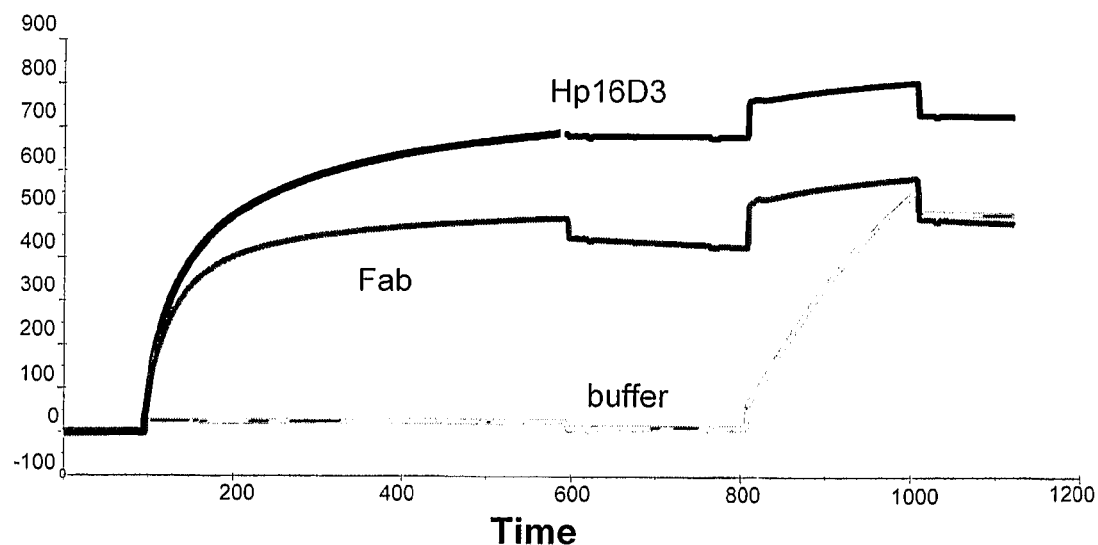
FIG. 3: Results of the Biacore experiments wherein rhuPlGF-2 is immobilized on a CM5 chip in order to investigate the inhibition potential of the antibody 16D3 and its Fab fragment test in accordance with an embodiment of the present invention.

Compared to the maximum binding of the rhuFlt-1 to the rhuPlGF-2, the signal of rhuFlt-1 is reduced if first 16D3 or 16D3Fab is injected (FIG. 3)

6. Cloning and Sequencing of the Mouse Variable Regions of 16D3 mRNA isolation: The mRNA of hybridoma cells of 16D3 was isolated using the QuickPrep™ Micro mRNA Purification Kit (Amersham Biosciences). This mRNA was used to make cDNA using the First-Strand cDNA Synthesis Kit (Amersham Biosciences) with the pd(N)$_6$ primer available in the kit.

PCR: The sequences of the variable parts of the heavy and the light chain were found by doing a PCR with a collection of primers: 8 primers starting in the leader sequence and 2 in the constant region of the heavy chain, 11 primers starting in the leader sequence and 1 in the constant region of the light chain. 8 and 11 PCR reactions with different combinations of the primers were performed.

primers used for the heavy chain of the antibody 16D3:

(SEQ ID NO: 9)
MHVR3  5'-ATG GRA TGG AGC TGK ATC WTT HTC-3'

(SEQ ID NO: 10)
MHCR1  5'-CAS AYM CAG GGG CCA GTG GAT AGA C-3' primers used for the light chain of the antibody 16D3:

(SEQ ID NO: 11)
MKVR3  5'- ATG RAG TCA CAK ACY CAG GTC TTY RTA-3'

(SEQ ID NO: 12)
MKCR1  5'- GCT CAC TGG ATG GTG GGA AGA TGG-3'

PCR set-up: denaturation 10 min. 94° C., denaturation 30s 94° C., annealing 30s 55° C., prolongation 1 min. 72° C., prolongation 5 min. 72° C., number of cycles 30.

The redundancy in the sequence of SEQ ID NO: 9 to 11 is indicated using the conventional abbreviations R=A or G, K=G or T, W=A or T, H=A or C or T, S=C or G, Y=C or T, M=A or C.

Cloning and sequencing: The PCR products were loaded on an agarose gel, the right bands were selected, purified (QIAquick® Gel Extraction kit, Qiagen GmbH) and cloned in pCR® 4Blunt-TOPO® vector supplied in the Zero Blunt® TOPO® PCR Cloning Kit for Sequencing (Invitrogen™ life technologies). Plasmid DNA was prepared using the High Pure Plasmid Isolation Kit (Roche Diagnostics GmbH) and the inserts were sequenced using the T7 and M13 reverse primers on the ABI PRISM™ 310 (PE Applied Biosystems).

The nucleotide and amino acid sequences of the variable regions of the heavy and light chains of antibody 16D3 are depicted in SEQ ID Nos 1, 2, 3 and 4. (see FIG. 11)

Example 2

Production and Characterization of Humanized Anti-Human PlGF Antibodies (16D3)

1. Construction of Humanized 16D3

Humanization of the Variable Regions

Mutations: The following mutations were made in order to humanize the variable parts of the mouse antibody 16D3:

Heavy chain:
I2V
P9A
K40A
T111L

Light chain:
S5T
S9D
A15L
K18R
R22N
L89V

The mutations were made by using the QuickChange® Multi Site-Directed Mutagenesis Kit (Stratagene®). 1 to 5 primers containing the mutations could be used in 1 PCR. After transformation colonies were picked and the DNA sequenced to determine the clone with the most point mutations. This clone was taken to repeat this procedure till all the mutations were present in the sequence.

Linking the Variable Regions to a Human IgG Constant Region:

By performing a PCR the humanized variable parts of the heavy and light chain were obtained to which the appropriate restriction sites were added.

Primers for the variable part of the light chain:

```
Primer 1:                              (SEQ ID NO: 13)
5'-CCACCGGT GAC ATT GTG CTG ACC CAG TCT CC-3'

Primer 2:                              (SEQ ID NO: 14)
5'-CACCGTACG TTT TAT TTC CAA CTT TGT CCC CGA G-3'
```

Primers for the variable part of the heavy chain:

```
Primer 3:                              (SEQ ID NO: 15)
5'-CAG GTC CAG CTG CAG CAG TCT G-3'

Primer 4:                              (SEQ ID NO: 16)
5'-GATGGGCCCTTGGTCGACGC TGA GGA GAC TGT GAG CAG
GG-3'
```

PCR set-up: denaturation 5 min. 94° C., denaturation 30s 94° C., annealing 30s 60° C., prolongation 30s 72° C., prolongation 5 min. 72° C., number of cycles 25.

The PCR products were loaded on an agarose gel, the bands were selected and purified (QIAquick® Gel Extraction kit, Qiagen GmbH). The PCR product of the variable part of the heavy chain of 16D3 was digested with SalI, the vector pKANEO-MCS50-Hleu-var #24 containing the complete constant part of the heavy chain of a human antibody (IgG4), with Eco47III and SalI and ligated. The PCR product of the variable part of the light chain was first cloned in pCR®4Blunt-TOPO® vector supplied in the Zero Blunt® TOPO® PCR Cloning Kit for Sequencing (Invitrogen™ life technologies). The variable part of the light chain was cut out by AgeI and BsiWI and cloned into the vector pKANEO-CM30-L-var #7 that already contained the constant part of a human kappa light chain. Both vectors were assembled to one vector by taking the expression cassette of the light chain out of the vector using PmeI and PacI and adding it to the vector containing the heavy chain.

The nucleotide and amino acid sequences of the variable parts of the heavy and light chains of the humanized antibody 16D3 are represented in SEQ ID No 5, 6, 7 and 8. (see FIG. 12)

2. Transient Expression of Hu16D3

Hu16D3 IgG4κ was transiently expressed in HEK 293 cells using the FreeStyle 293 Expression System (Invitrogen) according to the manufacturers instruction. Hu16D3 was purified from the supernatant using affinity chromatography on proSep vA Ultra. Purified hu16D3 was checked for purity by SDS-PAGE under reducing and non-reducing conditions. Hu16D3 was further tested for binding to huPlGF and for inhibition of the HuPlGF/huFLT-1 binding via ELISA (see FIGS. 1 and 2).

Example 3

In Vivo Investigation of the Inhibition of Tumor Growth with Anti-PLGF Antibodies 1. General Description of Materials and Methods Cell Culture The murine pancreatic cell lines Panc02 and the human pancreatic cell line DanG are a kind gift of S. Rosewicz (Charité-Universitätsmedizin Berlin, Germany). The human breast MDA-MB, colon LOVO and melanoma Mel2a cell line were obtained from the American Type Culture Collection (ATCC; Manassas, Va., USA). All cells were cultured as recommended. Murine 16D3 anti-PlGF antibodies were used for all in vivo experiments, to avoid immune reaction to the antibody.

Animal Experiments

All animal procedures were fully approved by the institutional animal care and use committee. Female NMRI nu/nu mice were housed under semi-sterile conditions and were routinely used at 8-10 weeks of age (approximate weight, 25 g). For the preparation of tumor source, tumor cells were trypsinized to prepare single-cell suspension, washed with PBS. The centrifuged pellet, was re-suspended in 200 µl PBS and injected subcutaneously into the right flank of the mice. For the orthotopic pancreatic tumor model, $1 \times 10^6$ tumor cells in 30 µl PBS were injected into the head of the pancreas via ventral laparotomy of female C57B16 mice at the age of 9-10 weeks. Before the procedures, mice were anesthetized with ketamine (90 mg/kg body weight) and xylazine (9 mg/kg body weight).

Administration of Drugs (i.e. Antibodies, Vehicle, Etc.)

Treatment with antibodies or vehicle control was initiated when tumors reached a size of approximate 60 mm³. Antibodies P15D11D4 (WO01/85796), 16D3, 1C8 or vehicle were administered at the indicated doses intraperitoneally every other day. Avastin was injected at the indicated doses intraperitoneally twice a week.

Measurements of Tumors

Subcutaneously growing tumors were measured every other day using a caliber, and tumor volumes calculated using the formula p/6 (w1×w2×w2), where 'w1' and 'w2' represent the largest and smallest tumor diameter, respectively. When mice were sacrificed orthotopic growing tumors of the pancreas were measured after ventral laparotomy using the same method.

Statistical Analysis

Statistical analysis was performed by two-tailed Student t-test for paired observations using GraphPad statistical software (GraphPad Software Inc., San-Diego, Calif.). All data are expressed as mean±SEM, unless otherwise indicated. *p<0.5, **p<0.01, unless otherwise indicated.

2. Inhibition of Tumor Growth in a Subcutaneous Human Pancreatic DanG Xenograft Tumor Model with the Murine Anti-hPlGF Antibody 16D3.

$1 \times 10^6$ tumor cells were subcutaneously injected into the right flank of 11 weeks old female NMRI nu/nu mice. After tumors reached a size of approximately 60 mm³, treatment with anti-hPlGF (16D3, 50 mg/kg body weight; n=10), anti-mPlGF (PL5D11D4 (obtained as described in WO01/85796; 50 mg/kg body weight; n=10), control IgG (1C8; 50 mg/kg body weight; n=10), a combination of anti-hPlGF and anti-mPlGF (each 25 mg/kg body weight; n=10) and vehicle (n=10) was started. Antibodies were injected i.p. every other day. (A) Tumors were measured every other day and tumor volume calculated using the formula W1×W2×W2×p/2, whereby W1 represents the longest and W2 the smallest diameter. (B) Mice were sacrificed at day 18 after tumor inoculation, tumors resected and weighted. Mean tumor volume: vehicle: 915±90 mm³, IgG: ±89 mm³, PL5D11D4: 832±118 mm³, 16D3: 521±83 mm³, PL5D11D4+16D3: 497±86 mm³.

The results, as shown in FIG. 4, show that the administration of anti-human PLGF antibody 16D3 has a clear influence on the tumor weight and size.

3. Anti-hPlGF Inhibits Tumor Growth in a Subcutaneous Human Pancreatic DanG Xenograft Tumor Model in a Dose Dependent Manner.

$1 \times 10^6$ tumor cells were subcutaneously injected into the right flank of 11 weeks old female NMRI nu/nu mice. After tumors reached a size of approximately 60 mm3, treatment with anti-hPlGF, IgG (1C8; 50 mg/kg), 16D3 (50 mg/kg, 37.5 mg/kg, 25 mg/kg, 12.5 mg/kg body weight; n=10 for each concentration) and vehicle (n=10). (B) Mice were sacrificed at day 18 after tumor inoculation.

The results are shown in FIG. 5. Mean tumor volume±SEM: 16D3, 50 mg/kg body weight: 450±37 mm³; 37.5 mg/kg body weight: 469±97 mm³; 25 mg/kg body weight: 493±107 mm³; 12.5 mg/kg body weight: 693±107 mm³; IC8: 865±109 mm³; vehicle: 889±100 mm³.

4. Anti-huPlGF Inhibits Tumor Growth in a Subcutaneous Human Breast MDA-MB Xenograft Tumor Model.

$1 \times 10^7$ tumor cells were subcutaneously injected into the right flank of 11 weeks old female NMRI nu/nu mice. After tumors reached a size of approximately 60 mm3, treatment with anti-hPlGF, 16D3 (50 mg/kg body weight; n=10) and vehicle (n=10).

The results are shown in FIG. 6 (and Table 1 below).

TABLE 1

|  | Mean | SEM | N | P value |
| --- | --- | --- | --- | --- |
| TM weight PBS | 1086 | 154.1 | 10 |  |
| TM weight 16D3 | 586.6 | 71.89 | 10 | 0.0088 |
| TM size PBS | 991.5 | 160.8 | 10 |  |
| TM size 16D3 | 485.9 | 63.76 | 10 | 0.0091 |

5. Anti-huPlGF Inhibits Tumour Growth in a Subcutaneous Human Colon LOVO Xenograft Tumour Model.

$1 \times 10^7$ tumor cells were subcutaneously injected into the right flank of 11 weeks old female NMRI nu/nu mice. After tumors reached a size of approximately 60 mm3, treatment with anti-hPlGF, 16D3 (50 mg/kg body weight; n=10) and vehicle (n=10).

The results are shown in FIG. 7 and Table 2 below.

TABLE 2

|  | Mean | SEM | N | P value |
| --- | --- | --- | --- | --- |
| TM weight PBS | 669.3 | 103 | 10 |  |
| TM weight 16D3 | 415 | 65.85 | 10 | 0.052 |
| TM size PBS | 568.3 | 95.38 | 10 |  |
| TM size 16D3 | 306.4 | 50.27 | 10 | 0.0258 |

6. Anti-huPlGF Inhibits Tumour Growth in a Subcutaneous Human Melanoma Mel2a Xenograft Tumour Model.

$4 \times 10^6$ tumor cells were subcutaneously injected into the right flank of 11 weeks old female NMRI nu/nu mice. After tumors reached a size of approximately 60 mm3, treatment with anti-hPlGF, 16D3 (50 mg/kg body weight; n=10) and vehicle (n=10).

Figure 8:
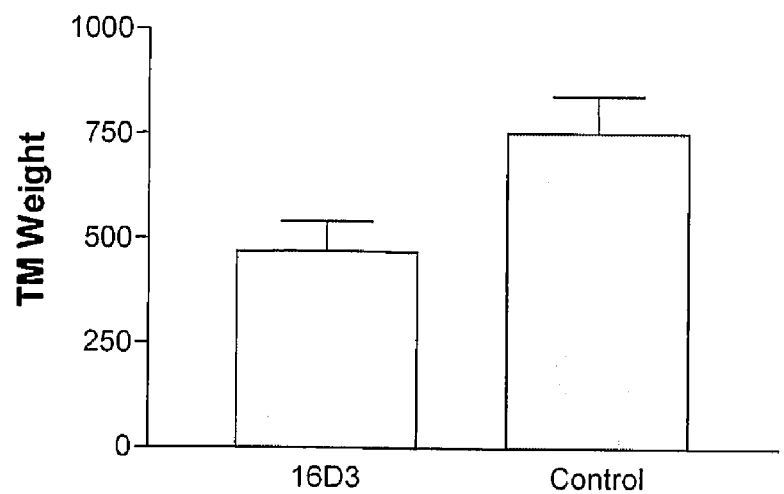
FIG. 8: Monoclonal antibody 16D3 inhibits tumor growth in a subcutaneous human melanoma Mel2a xenograft tumor model. Treatment of nu/nu mice with tumors of approximately 60 mm$^3$ with anti-hPlGF 16D3 (50 mg/kg body weight; n=10) or vehicle three times a week in accordance with an embodiment of the present invention. Tumor weight as determined 53 days post inoculation.

The results are shown in FIG. 8 and Table 3 below.

TABLE 3

|  | Mean | SEM | N | P value |
| --- | --- | --- | --- | --- |
| TM weight PBS | 753.3 | 87.26 | 10 |  |
| TM weight 16D3 | 468.9 | 70.57 | 9 | 0.023 |

Example 4

In Vivo Investigation of Effect of the Treatment with 16D3 Antibodies on Weight Loss Materials and Methods were as Described for Example 3.

$1 \times 10^6$ tumor cells were subcutaneously injected into the right flank of 11 weeks old female NMRI nu/nu mice. After tumors reached a size of approximately 60 mm3, treatment with anti-hPlGF (16D3, 50 mg/kg body weight; n=10), anti-mPlGF (PL5D11D4; 50 mg/kg body weight; n=10), control IgG (1C8; 50 mg/kg body weight; n=10), a combination of anti-hPlGF and anti-mPlGF (each 25 mg/kg body weight; n=10) and vehicle (n=10) was started. Antibodies were injected i.p. every other day. Body weight of mice was measured at the first and last day of antibody treatment. Tumor weight was subtracted from body weight prior to calculation of the percentage of body weight loss.

Figure 9:
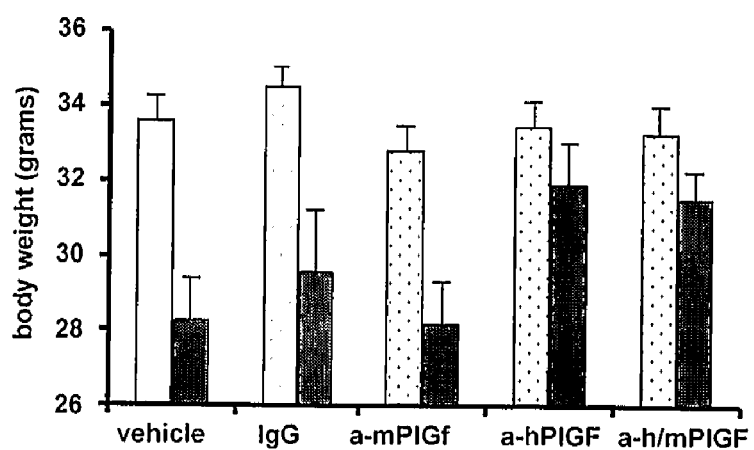
FIG. 9: Monoclonal antibody 16D3 prevents body weight loss in a subcutaneous human pancreatic DanG xenograft tumor model. Treatment of nu/nu mice with tumors of approximately 60 mm$^3$ with anti-hPlGF 16D3 (50 mg/kg body weight; n=10), control IgG, a combination of anti-hPlGF and anti-mPlGF (each 25 mg/kg body weight; n=10) and vehicle (n=10) in accordance with an embodiment of the present invention. Tumor weight was subtracted from body weight prior to calculation of the percentage of body weight loss. Open bars: body weight on first day of treatment; filled bars: body weight on last day of treatment

The results are shown in FIG. 9. It is shown that anti-hPlGF prevents body weight loss in this subcutaneous human pancreatic DanG xenograft tumor model.

Example 5

Combination of Anti-hPlGF and an Anti-VEGF Antibody for the Treatment of Tumor Growth Materials and Methods were as Described for Example 3.

$1\times10^6$ tumor cells were subcutaneously injected into the right flank of 11 weeks old female NMRI nu/nu mice. After tumors reached a size of approximately 60 mm3, treatment with anti-hPlGF (16D3, 50 mg/kg, 37.5 mg/kg, 12.5 mg/kg body weight i.p. every other day; n=10 for each concentration), Avastin (15 mg/kg and 5 mg/kg body weight, i.p. twice weekly, n=10 each) and a combination of anti-hPlGF (12.5 mg/kg body weight) and Avastin (5 mg/kg body weight; n=10). Mice were sacrificed after 20 days of tumor inoculation.

Figure 10:
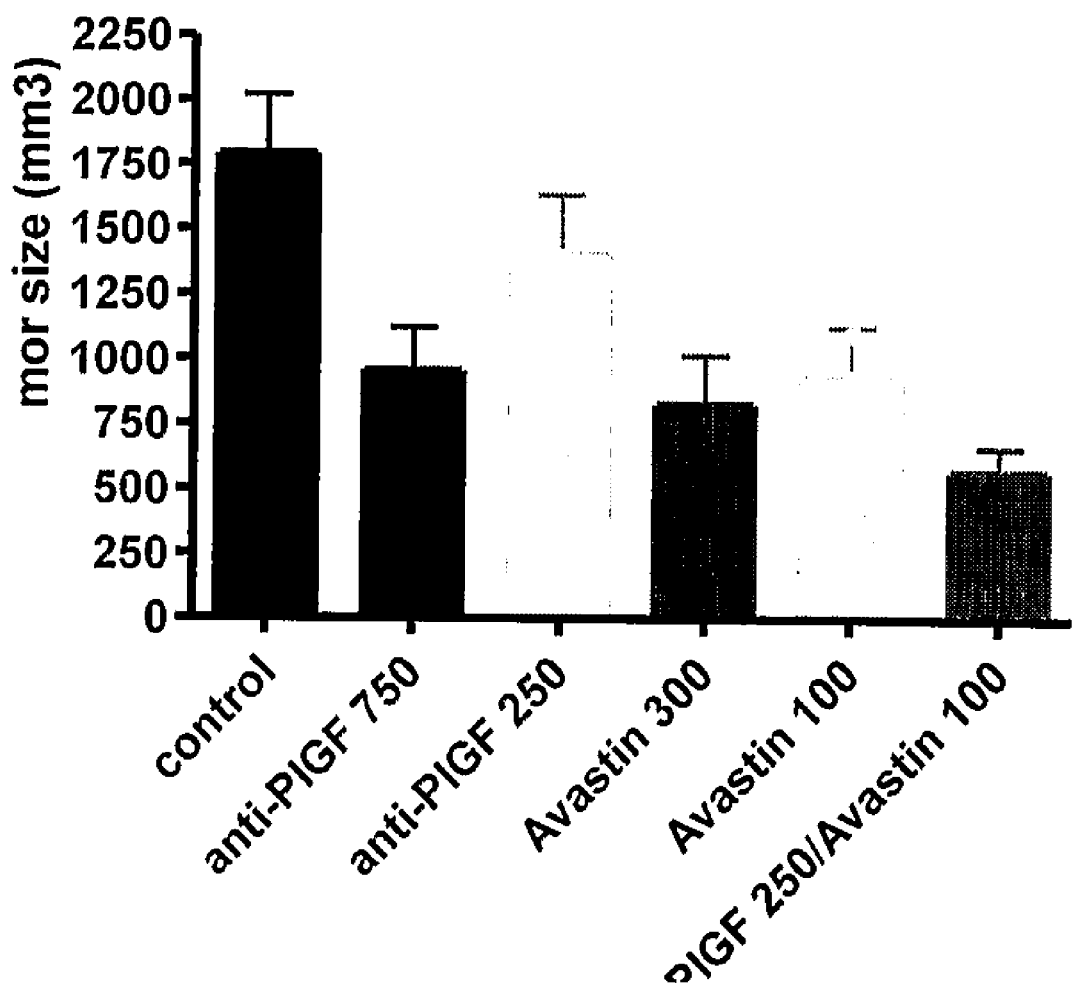
FIG. 10: Monoclonal antibody 16D3 and Avastin exert additional effect on inhibition of tumor growth in a subcutaneous human pancreatic DanG. Treatment of nu/nu mice with tumors of approximately 60 mm$^3$ with anti-hPlGF 16D3 (37.5 mg/kg, 25 mg/kg, 12.5 mg/kg body weight; n=10 for each concentration), control IgG (1C8; 50 mg/kg), Avastin (15 mg/kg and 5 mg/kg body weight, i.p. twice weekly, n=10 each) and a combination of anti-hPlGF (12.5 mg/kg body weight) and Avastin (5 mg/kg body weight; n=10) in accordance with an embodiment of the present invention. Mice were sacrificed after 20 days of tumor inoculation and tumor volume was determined.

The results are shown in FIG. 10. Mean tumor volume±SEM: 1C8, 37; 37.5 mg/kg body weight: 954±164 mm$^3$; 12.5 mg/kg body weight: 1398±236 mm$^3$; IgG: 1789±231 mm$^3$; Avastin: 15 mg/kg body weight: 828±186 mm$^3$; 5 mg/kg body weight: 926±202 mm$^3$; Avastin+16D3: 569±94 mm$^3$. It is observed that anti-hPlGF and Avastin exert additional effect on inhibition of tumor growth in a subcutaneous human pancreatic DanG.

Example 6

Production of scFv of 16D3

The sequences of the variable parts of the heavy and light chain (SEQ IDs NO: 2 and 4, respectively, obtained as described in Example 1) were amplified by PCR using primers with the appropriate restriction binding sites and linker. After a SOE PCR (gene splicing by overlap extension) the scFv was cloned in pEE14.4 (HindIII-EcoRI cloning sites) (FIG. 12).

Figure 13:
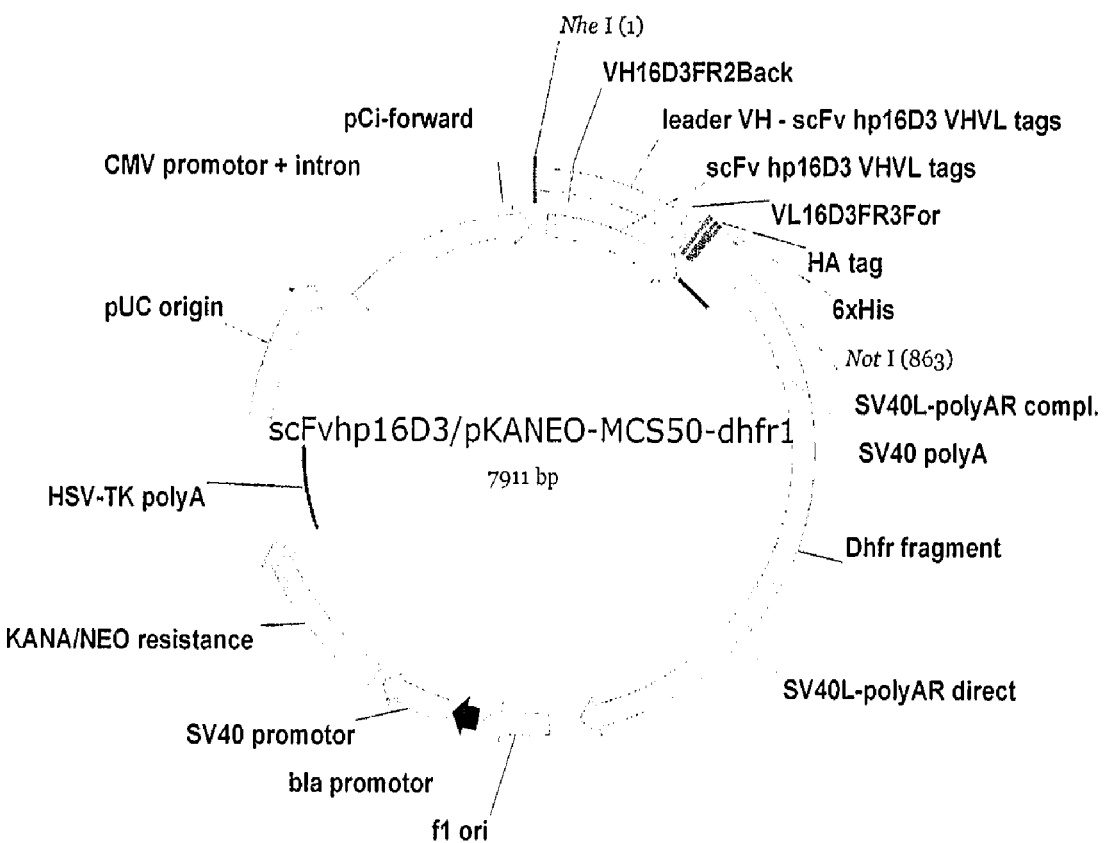
FIG. 13: Illustration of the vector for expression of humanized 16D3 scFv in 293 cells

This scFvhp16D3/pEE14.4 was transfected to CHO-KI cells after linearisation with BamHI using Fugene 6 (Boehringer Mannheim) and twice subcloned by dilution. A monoclonal scFv hp16D3, 6C5D4, was obtained and produced. This clone was also transiently transfected in 293 cells by Producell in parallel with scFv hp16D3/pKANEO-MCS50-dhfr1 (NheI-NotI cloning sites) (FIG. 13).

The nucleotide and amino acid sequence of the 16D3 scFv are provided as SEQ ID NO: 23 and SEQ ID NO: 24, respectively. The amino acid sequence demonstrating the heavy and light chain variable regions, the linker sequence and the HA-tag and His Tag is also provided in FIG. 15.

Example 7

Humanization of scFv 16D3

Humanization of the variable regions of the scFv was performed as described in Example 2. The nucleotide and amino acid sequences of the humanized scFv of 16D3 are provided in SEQ ID NO:25 and SEQ ID NO:26, respectively. The amino acid sequence demonstrating the heavy and light chain variable regions, the linker sequence and the HA-tag and His Tag of the humanized scFv is also provided in FIG. 15.

Example 8

Production of Humanized Fab 16D3

1. Amplifying the VH and VL Fragments from Humanized scFv16D3

Primers for Amplification VH Fragment of Humanized scFv16D3

```
16D3Vhbackblunt                      (SEQ ID NO: 27)
5'-CAGGTCCAGCTGCAGCAGTCTG-3'

16D3VhforSalI                        (SEQ ID NO: 28)
5'-GATGGGCCCTTGGTCGACGCTGAGGAGACTGTGAGCAGGG-3'
```

Primers for Amplification of VL Fragment of Humanized scFv16D3

```
16D3VLBackAgeI                       (SEQ ID NO: 29)
5'-CCACCGGTGACATTGTGCTGACCCAGTCTCC-3'

16D3VLForBsiWI                       (SEQ ID NO: 30)
5'-CACCGTACGTTTTATTTCCAACTTTGTCCCCGAG-3'
```

2. Construction of Heavy and Light Chain Vectors

The PCR product of the light chain was first cloned into pCR4blunt-TOPO vector. After sequencing the light chain was removed by AgeI and BsiWI digestion and cloned into the pKANEO-CM30-Lvar#7 vector. The PCR product of the heavy chain was after digestion cloned directly in pKANEO-MCS50-Fabvar#3.

3. Joining of Heavy and Light Chain Constructs

Figure 16:
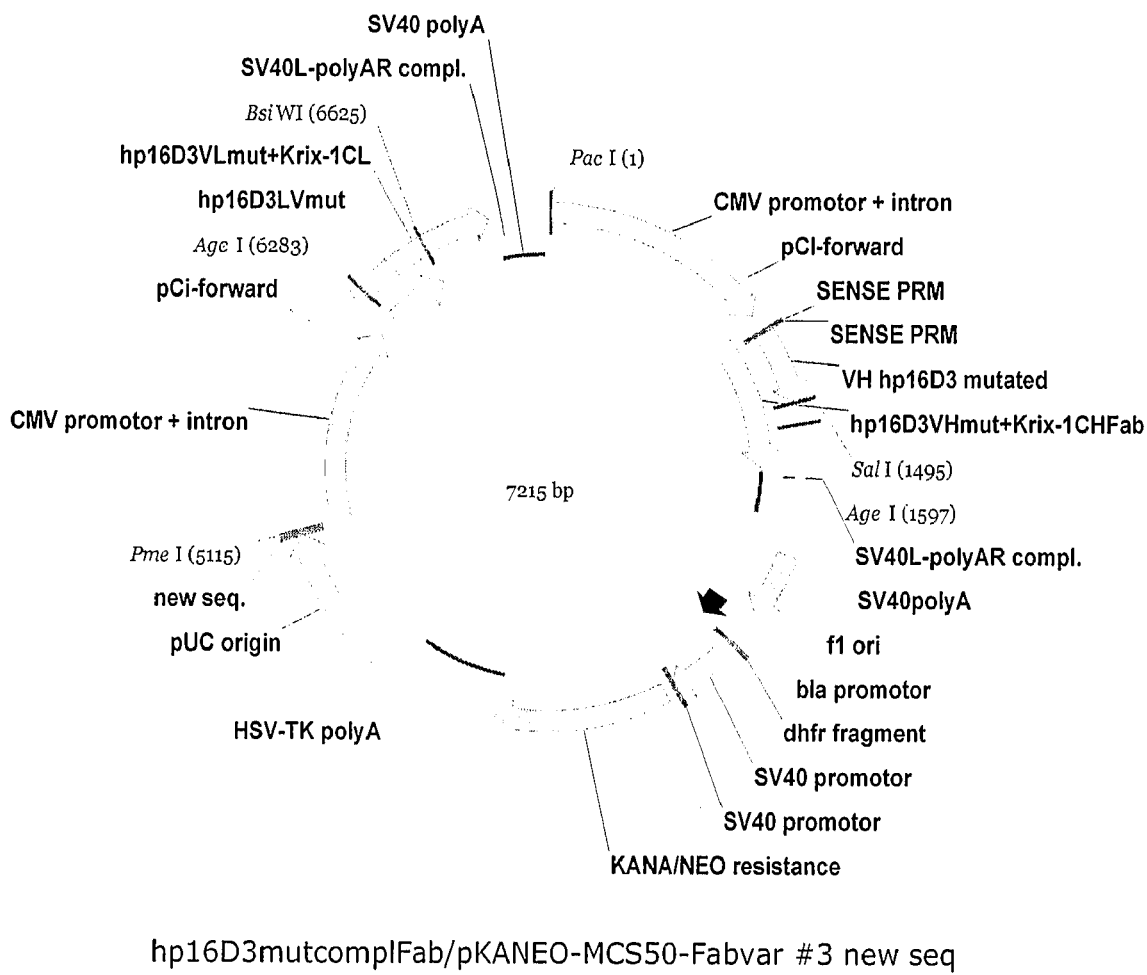
FIG. 16: Illustration of the vector for expression of humanized 16D3 Fab in 293 cells in accordance with an embodiment of the invention.

Both vectors (described above), containing the light and heavy segment, were joined together by removing the cassette containing the light segment and adding it to the vector containing the heavy segment by using the enzymes PmeI and PacI, to obtain the final construct, hp16D3mutcmplFab/pKANEO-MCS50-Fabvar#3. (see FIG. 16)

Example 9

Analysis of Antigen Binding and Inhibition of PlGF/flt-1 Interaction by scFv 16D3 And Humanized scFv 16D3. (FIG. 14)

1. Antigen Binding ELISA

ELISA plates were coated ON with 1 μg/ml huPlGF-1 in PBS, 200 μL/well, 4° C. After blocking with 1% BSA, 1 hr, RT, a dilution series of scFv16D3/humanized scFv16D3 was added, 200 μL/well, the antibody fragment was allowed to bind for 1 hr, RT. Bound scFv16D3 was detected with murine anti-HA (180 μL/well, 1 hr RT) followed by incubation with goat-anti-murine IgG-HRP (Sigma), 170 μL/well, 1 hr, RT. The assay was developed with OPD.

2. Inhibition of PlGF/Flt-1 Interaction Via ELISA

ELISA plates were coated ON with 1 μg/ml huFlt-1 (R&D Systems), 200 μL/well, ON, 4° C. After blocking with 1% B SA, 1 hr, RT, a dilution series of scFv 16D3/humanized scFv 16D3 was added, 100 μL/well, and an additional 100 μL/well of huPlGF-2 was added. After a 2 hour incubation at RT, bound PlGF was detected with Goat-anti-huPlGF (R&D Systems), 180 μL/well, 1 hr, RT, followed by an incubation with RAG-HRP (DAKO), 1 hr, RT. The assay was developed with OPD.

Example 10

Analysis of Antigen Binding and Inhibition of PlGF/Flt-1 Interaction by Humanized Fab16D3

1. Antigen Binding ELISA

ELISA plates were coated ON with 1 μg/ml huPlGF-1 in PBS, 100 μL/well, 4° C. After blocking with 1% BSA, 1 hr, RT, a dilution series of humanized Fab16D3 was added, 100 μL/well, the antibody fragment was allowed to bind for 1 hr, RT. Bound humanized Fab16D3 was detected with anti-huIgG-HRP (Fab specific) (100 μL/well, 1 hr RT). The assay was developed with OPD. The results are provided in FIG. 17A 2. Inhibition of PlGF/Flt-1 Interaction Via ELISA ELISA plates were coated ON with 1 μg/ml huFlt-1 (R&D Systems), 200 μL/well, ON, 4° C. After blocking with 1% BSA, 1 hr, RT, a dilution series of humanized Fab 16D3 was added, 100 μL/well, and an additional 100 μL/well of huPlGF-2 was added. After a 2 hour incubation at RT, bound PlGF was detected with Goat-anti-huPlGF (R&D Systems), 180 μL/well, 1 hr, RT, followed by an incubation with RAG-HRP (DAKO), 1 hr, RT. The assay was developed with OPD. The results are provided in FIG. 17B.

Example 11

Determination of $K_D$ Values

The $K_D$ values for 16D3, humanized 16D3 IgG4, humanized scFv16D3 and humanized Fab16D3 were determined by Biacore. The results are provided in Table 4 below.

TABLE 4

| Summary table of $K_D$ values. | | |
|---|---|---|
| immobilized protein | injected antibody | $K_D$ (M) |
| rhuPlGF-2 *Pichia* | scFvhp16D3mut | 1.95E−10 |
| rhuPlGF-2 *Pichia* | hp16D3mousecomplAB | 2.90E−10 |
| rhuPlGF-2 *Pichia* | hp16D3mutcomplABIgG4 | 1.61E−10 |
| rhuPlGF-2 *Pichia* | hp16D3mutcomplFab | 1.31E−10 |

$K_D$ values of 16D3, humanized 16D3 IgG4, humanized Fab 16D3 and humanized scFv16D3.

The invention claimed is:

1. An isolated antibody capable of binding to human PlGF or an antigen-binding fragment of said antibody, wherein said antibody comprises a variable heavy chain sequence of which the sequence of the CDR1, CDR2, and CDR3 region corresponds to the sequence of SEQ ID NO: 17, 18, and 19, respectively, and comprises a variable light chain sequence of which the sequence of the CDR1, CDR2, and CDR3 region corresponds to the sequence of SEQ ID NO: 20, 21, and 22, respectively.

2. The antigen-binding fragment according to claim 1, which is selected from the group consisting of a Fab, Fab', and F(ab')2.

3. The antibody according to claim 1, comprising a variable heavy chain comprising the sequence of SEQ ID NO:2 or a sequence having at least 95% sequence identity therewith outside the CDR regions and comprising a variable light chain comprising the sequence of SEQ ID NO:4 or a sequence having at least 95% sequence identity therewith outside the CDR regions.

4. The antibody according to claim 1, which is the antibody 16D3 as produced by the cell line deposited as LMBP 6399CB.

5. The antibody or antigen-binding fragment of said antibody according to claim 1, which is a humanized antibody or antigen binding fragment thereof.

6. The antibody or antigen-binding fragment of said antibody of claim 1, which comprises the amino acid sequence of SEQ ID NO:24.

7. The antibody or antigen-binding fragment of said antibody of claim 1, which comprises the amino acid sequence of SEQ ID NO:26.

8. A cell line producing an antibody according to claim 1.

9. The cell line according to claim 8, which is the cell line deposited as LMBP 6399CB.

10. A pharmaceutical composition, comprising as an active ingredient an antibody or antigen-binding fragment of said antibody according to claim 1 in an admixture with a pharmaceutically acceptable carrier.

11. The pharmaceutical composition according to claim 10, further comprising a therapeutically effective amount of another anti-angiogenic agent.

12. A method of treatment of undesired angiogenesis in a pathological condition in a mammal, comprising administering to a mammal in need of such treatment a therapeutically effective amount of an antibody or an antigen-binding fragment of said antibody according to claim 1.

13. The method according to claim 12, wherein the pathological condition is selected from the group consisting of cancer, inflammation, adhesion formation, diseases of the eye, pulmonary hypertension and vascular leakage.

14. The method of claim 13, wherein said cancer is selected from the group consisting of colon cancer, breast cancer, pancreatic cancer, and melanomas.

15. A method of immunological detection of PlGF in human samples comprising contacting a human sample with the antibody or antigen-binding fragment of said antibody of claim 1, and detecting the binding of said antibody or antigen-binding fragment of said antibody.

16. A method of screening for compounds with an additive effect to PlGF inhibition in the treatment of cancer, comprising administering to an animal tumor model an antibody or antigen-binding fragment of said antibody of claim 1 and a test compound, and identifying whether the compound has an additive effect to the effect observed upon administration of the antibody or antigen-binding fragment of said antibody.

17. The antigen-binding fragment according to claim 1, which is an antigen-binding fragment of the antibody 16D3 as produced by the cell line deposited as LMBP 6399CB.

* * * * *

UNITED STATES PATENT AND TRADEMARK OFFICE
CERTIFICATE OF CORRECTION

PATENT NO. : 7,875,704 B2  Page 1 of 1
APPLICATION NO. : 11/909604
DATED : January 25, 2011
INVENTOR(S) : Stassen et al.

It is certified that error appears in the above-identified patent and that said Letters Patent is hereby corrected as shown below:

Column 12, line 20, replace "12V" with
-- I2V --.

Column 12, line 31, replace "12V" with
-- I2V --.

Column 19, line 18, replace "alt" with
-- art --.

Signed and Sealed this
Seventh Day of June, 2011

David J. Kappos
*Director of the United States Patent and Trademark Office*